US012599345B2

(12) United States Patent (10) Patent No.: US 12,599,345 B2

Reid et al. (45) Date of Patent: Apr. 14, 2026

(54) SUPPORT APPARATUS, SYSTEM, AND METHOD FOR POSITIONING A PATIENT

(71) Applicant: Qfix Systems, LLC, Avondale, PA (US)

(72) Inventors: Melissa Reid, Newark, DE (US); Sean F. McGrenaghan, West Chester, PA (US); Mathew Michael Gordon, Drexel Hill, PA (US); David Martin Rabeno, Avondale, PA (US)

(73) Assignee: Qfix Systems, LLC, Avondale, PA (US)

( * ) Notice: Subject to any disclaimer, the term of this patent is extended or adjusted under 35 U.S.C. 154(b) by 922 days.

(21) Appl. No.: 17/642,012

(22) PCT Filed: Sep. 14, 2020

(86) PCT No.: PCT/US2020/050747

§ 371 (c)(1),
(2) Date: Mar. 10, 2022

(87) PCT Pub. No.: WO2021/051090

PCT Pub. Date: Mar. 18, 2021

(65) Prior Publication Data

US 2022/0378386 A1 Dec. 1, 2022

Related U.S. Application Data

(60) Provisional application No. 62/900,607, filed on Sep. 15, 2019.

(51) Int. Cl.
A61B 6/04 (2006.01)
A61N 5/10 (2006.01)

(52) U.S. Cl.
CPC .......... A61B 6/0421 (2013.01); A61B 6/0492 (2013.01); *A61N 2005/1097* (2013.01)

(58) Field of Classification Search
CPC ..... A61B 6/0492; A61B 6/0421; A61B 5/055; A61B 5/702; A61B 6/032; A61B 6/037;
(Continued)

(56) References Cited

U.S. PATENT DOCUMENTS 4,166,459 A * 9/1979 Nightingale ......... A61H 1/0218
5/636
4,615,516 A * 10/1986 Stulberg ................. A61G 13/12
5/651
(Continued)

FOREIGN PATENT DOCUMENTS

EP 3517173 A1 7/2019
WO WO-2008114050 A1 * 9/2008 ............. A61G 15/12

OTHER PUBLICATIONS

International Search Report and Written Opinion for International Application No. PCT/US2020/050747, dated Dec. 4, 2020, 11 pages.
(Continued)

*Primary Examiner* — Matthew Troutman
*Assistant Examiner* — Alison N Labarge
(74) *Attorney, Agent, or Firm* — Buchanan Ingersoll & Rooney PC

(57) ABSTRACT

A support system configured to support the lower extremities of a patient, for example during radiotherapy and imaging procedures, and methods for employing the same is provided. The support system includes a knee support apparatus and a foot support apparatus, each of which may be used together or independently in order to customize the support needed for the particular procedure. When used on the patient table of an appropriate imaging or treatment modality, the support system is configured to allow the clinician to independently adjust the knee support and foot support's positioning in the superior-inferior axis of the patient table in both a gross and fine manner for optimal (Continued)

positioning of the patient for the target procedure. The robust adjustment capabilities of the support system enable enhanced patient comfort, setup reproducibility, and workflow efficiency.

15 Claims, 15 Drawing Sheets

(58) Field of Classification Search
CPC ........ A61N 2005/1097; A61G 13/1245; A61G 13/12
See application file for complete search history.

(56)                          References Cited

U.S. PATENT DOCUMENTS

| | | | |
|---|---|---|---|
| 11,779,322 B2 * | 10/2023 | Garcia-Bengochea | ...................... A61B 17/025 600/215 |
| 2006/0248650 A1 * | 11/2006 | Skripps | .............. A61G 13/0054 5/624 |
| 2009/0308400 A1 * | 12/2009 | Wilson | ................... A61B 90/57 128/845 |
| 2016/0193098 A1 * | 7/2016 | Nichols | ................ A61G 13/121 602/32 |

OTHER PUBLICATIONS

International Preliminary Report on Patentability and Written Opinion for International Application No. PCT/US2020/050747, issued Mar. 15, 2022, 9 pages.

* cited by examiner

SUPPORT APPARATUS, SYSTEM, AND METHOD FOR POSITIONING A PATIENT

CROSS REFERENCE TO RELATED APPLICATIONS

This is the U.S. National Phase Application of PCT/US2020/50747, filed Sep. 14, 2020, which claims the benefit of priority of U.S. Provisional Application No. 62/900,607, filed on Sep. 15, 2019, the disclosures of each of these applications being incorporated by reference herein in their entirety for all purposes.

FIELD OF THE INVENTION

The present invention is directed to apparatus and a system configured to support the anatomy of a patient, for example during radiotherapy and imaging procedures, and methods for employing the same.

BACKGROUND OF THE INVENTION

Treatment of a patient undergoing radiotherapy often involves precise imaging and treatment procedures. Patients are typically imaged (or "simulated") on an imaging modality (including, but not limited to, X-ray, computed tomography (CT), magnetic resonance imaging (MRI), and positron emission tomography (PET)) to aid the clinician in determining appropriate treatment plans. Patients will then undergo treatment on a radiotherapy modality (including, but not limited to, linear accelerator (Linac), proton therapy, heavy ion therapy, and photon therapy). In some instances, the imaging and treatment modalities may be combined into one unit, as in commercially available combination MR imaging/linear accelerator systems (MR-Linac), which combine a magnetic resonance imaging system with an on-board linear accelerator to deliver treatment.

Regardless of the chosen imaging and/or treatment modalities, it is critical that the patient is positioned in the same position for treatment as they were initially imaged, as margins and dosages of radiation to the tumor or other target pathologies are determined based on the images obtained in simulation, with an eye to destroy the tumor or other target pathology while limiting incidental damage to healthy tissues as a result of treatment. In particular, in radiotherapy, patients often require multiple treatment sessions over a period of weeks, and it is required that the patient is set up in the same position from one session to the next. Also key to smooth, accurate simulation and treatment, is patient comfort, as a patient who is uncomfortable may not be able to tolerate a particular position for the duration of a scan or treatment and may, as a result, inadvertently shift their position in a manner that is detrimental to the treatment plan.

Because of this, a patient's anatomy may further require additional adjustment or manipulation to ensure the patient is in the appropriate position. This can be cumbersome, as existing positioning devices may lack precision or capability for fine adjustment and may further require the patient's anatomy to be lifted off or otherwise removed from the device. For larger anatomical regions such as the lower extremities or for patients with limited strength or mobility to assist in these adjustments, the clinician may face further difficulty with manipulating the patient anatomy, requiring significant time to reposition the patient, severely impacting workflow efficiency. Accordingly, there is a need for patient positioning aids or supports where large manipulations of patient anatomy are limited and finer adjustments to positioning are accommodated, thereby enhancing clinical workflows and patient comfort.

SUMMARY OF THE INVENTION

Aspects of the present invention are directed to apparatus and a system configured to support the anatomy of a patient, for example during radiotherapy and imaging procedures, and methods for employing the same.

In accordance with an aspect of the invention, a support apparatus is provided, configured to support the anatomy of a patient, for example during radiotherapy and imaging procedures. Said support apparatus includes at least one locator configured to removably locate to corresponding indexing structures of a patient table of an imaging or treatment modality. The support apparatus additionally includes at least one directional guide running parallel to a direction relative to the patient table, said directional guide having a set distance. The support apparatus further includes at least one shuttle configured to slidably adjust the support apparatus along the at least one directional guide. The support apparatus further includes a releasable lock configured to resist the motion of the at least one shuttle in a first engaged position and enable motion of the at least one shuttle in the direction of the at least one directional guide in a second disengaged position. The support apparatus is so configured such that a clinician may select the gross position of the support apparatus by locating the at least one indexing structure with the patient table of the imaging or treatment modality. If further fine adjustment of the patient's anatomy is desired, the clinician is able to disengage the releasable lock and slidably adjust the support apparatus along the direction of the directional guide, without the need to lift or remove the patient's anatomy from the support apparatus or disturb the gross position of the support apparatus. This support apparatus may further include features which adjust either the height of the support apparatus or the angle of the support apparatus, further accommodating additional fine adjustments to the position of the patient's anatomy. The at least one shuttle may also be configured to provide discrete adjustment increments along the direction of the at least one directional guide.

According to a second aspect of the invention, a support system is provided with a plurality of support devices, wherein at least one of the support devices is a support apparatus as described in the foregoing aspect of the present invention, with at least one support apparatus of the support system being capable of being adjusted with respect to at least one of gross position, fine adjustment, height, and/or angle of the patient's anatomy, which may further be independently adjusted.

In accordance with another aspect of the invention, the support apparatus is configured to support the lower extremities of a patient, for example a patient's knees or feet.

In accordance with one portion of this aspect of the invention, a knee support is provided which includes at least one support designed to support a patient's legs in the area surrounding the popliteal fossa. The knee support is further configured to accommodate at least one indexing structure which removably positions the knee support to the patient table of a modality. The knee support further includes at least one directional guide having a set distance running parallel to a direction relative to the patient table and at least one shuttle which allows the knee support to slidably adjust along the at least one directional guide. The knee support further includes at least one releasable lock configured to resist the motion of the at least one shuttle in a first engaged position and enable motion of the at least one shuttle in the direction of the at least one directional guide in second disengaged position. The knee support may also include a height adjustment feature. Further, the at least one shuttle may additionally be configured to provide discrete adjustment increments along the direction of the at least one directional guide. In another aspect of this aspect of this invention, independent adjustment of the directional position and/or height of each knee may be provided.

In accordance with another portion of this aspect of the invention, a foot support is provided which includes at least one support designed to support the patient's heels and soles of their feet. The foot support is further configured to accommodate at least one indexing structure which removably positions the foot support to the patient table of a modality. The foot support further includes at least one directional guide having a set distance running parallel to a direction relative to the patient table and at least one shuttle which allows the foot support to slidably adjust along the at least one directional guide. The foot support further includes at least one releasable lock configured to resist the motion of the at least one shuttle in a first engaged position and enable motion of the at least one shuttle in the direction of the at least one directional guide in second disengaged position. The foot support may also include an angular adjustment feature. Further, the at least one shuttle may additionally be configured to provide discrete adjustment increments along the direction of the at least one directional guide. In another aspect of this aspect of the invention, independent adjustment of directional position and/or angle of each foot may be provided.

In accordance with yet another aspect of the invention, a support system configured to support the anatomy of a patient, for example, the lower extremities of a patient is provided. An exemplary support system configured to support the lower extremities is described and includes both a knee support and foot support. The knee support and foot support may be used together or independently in order to customize the support needed for the particular procedure. Both the knee support and foot support are each configured to accommodate at least one indexing structure which removably positions the knee support to the patient table of a modality. The knee support includes at least one member designed to support a patient's legs in the area surrounding the popliteal fossa. The knee support further includes at least one directional guide having a set distance running parallel to a direction relative to the patient table and at least one shuttle which allows the knee support to slidably adjust along the at least one directional guide. The knee support further includes at least one releasable lock configured to resist the motion of the at least one shuttle in a first engaged position and enable motion of the at least one shuttle in the direction of the at least one directional guide in second disengaged position. The knee support may also include a height adjustment feature. Further, the at least one shuttle may additionally be configured to provide discrete adjustment increments along the direction of the at least one directional guide. The foot support is provided which includes at least one member designed to support the patient's heels and soles of their feet. The foot support includes an angular adjustment feature. The foot support may further include at least one directional guide having a set distance running parallel to a direction relative to the patient table, at least one shuttle which allows the foot support to slidably adjust along the at least one directional guide, and at least one releasable lock configured to resist the motion of the at least one shuttle in a first engaged position and enable motion of the at least one shuttle in the direction of the at least one directional guide in second disengaged position. Further, the at least one shuttle may additionally be configured to provide discrete adjustment increments along the direction of the at least one directional guide. In another aspect of this aspect of the invention, independent adjustment of the directional position of each knee and foot may be provided. Further, independent adjustment of the height of each knee and the angle of each foot may additionally be provided. A method of use of this support system configured to support the lower extremities of a patient is provided in accordance with still another aspect of the invention.

A support apparatus configured to support a patient's anatomy is provided. The support apparatus comprises:

at least one support configured to support a patient's anatomy;

at least one locator configured to removably locate the support apparatus to a patient table of a target modality;

at least one directional guide having a set distance of travel;

at least one shuttle coupled to the at least one support, configured to slidably adjust the support along the at least one directional guide;

at least one releasable lock configured to restrict movement of the at least one shuttle along the at least one directional guide in a first engaged configuration, and enable movement of the at least one shuttle along the at least one directional guide in a second disengaged configuration.

A gross position of the support apparatus may be selected by locating the at least one locator to a corresponding structure on the patient table of the target modality. A position of the support apparatus may be finely adjusted in discrete increments along the set distance of travel of the at least one directional guide. According to an embodiment, the position of the support apparatus may be capable of being finely adjusted with minimal manipulation of the patient's anatomy.

The at least one directional guide may be selected from the group consisting of a track, a rail, a rack, a slot, and combinations thereof. The at least one locator may be configured to receive at least one pin or at least one disc located on the target modality. The at least one locator may be configured to receive pins of a conventional locating bar. The at least one shuttle may incorporate a series of locating features spaced according to the discrete increments of fine adjustments along the set distance of travel of the at least one directional guide. The at least one releasable lock may incorporate a detent which interfaces with the locating features incorporated in the at least one shuttle. The detent of the at least one releasable lock inhibits the motion of the at least one shuttle when the at least one releasable lock is in the first engaged configuration and does not inhibit motion of the at least one shuttle when the at least one releasable lock is in the second disengaged configuration.

The at least one releasable lock may further comprise at least one tensioner configured to return the at least one releasable lock to the first engaged configuration from the second disengaged configuration. The at least one tensioner is selected from of the group consisting of a spring, an elastic band, a belt, and combinations thereof. The components of the support apparatus may be composed of materials which are compatible with a magnetic resonance imaging (MRI) environment.

The support apparatus may additionally be capable of height adjustment. The support apparatus may additionally be capable of adjusting an angle of a patient's anatomy. The support apparatus may be configured to support the lower extremities of the patient. The support apparatus may be configured to support at least one of the knee or the foot of the patient.

A knee support comprising the following components is provided.

at least one support configured to support the patient's legs at an area around the popliteal fossa;

at least one locator configured to locate the knee support to a patient table of a target modality;

at least one directional guide having a set distance of travel;

at least one shuttle coupled to the at least one support, configured to slidably adjust the support along the at least one directional guide;

at least one releasable lock configured to restrict the movement of the at least one shuttle along the at least one directional guide in a first engaged configuration, and enable movement of the at least one shuttle along the at least one directional guide in a second disengaged configuration, wherein a gross position of the support is selected by locating the at least one locator to a corresponding structure on a patient table of a target modality and wherein the position of the support may be further finely adjusted in discrete increments along the set distance of travel of the at least one directional guide.

The knee support may further comprise at least one top portion. The top portion may be configured to support the patient's legs at the area around the popliteal fossa. The knee support may further support at least one base portion. The base portion may be removably attached to the at least one top portion, and may further be additionally coupled to the at least one directional guide, the at least one locator, the at least one shuttle, and the at least one releasable lock. The at least one base portion may be configured to be oriented in at least a first orientation and a second orientation. The at least one base portion may be configured such that it will be at a first height in the first orientation and at a second height in the second orientation. The knee support may be composed of materials which are compatible with a magnetic resonance imaging (MRI) environment. The at least one top portion of the knee support may comprise protrusions to be received by corresponding apertures in the at least one base portion.

The at least one shuttle of the knee support may have at least five discrete increments along the set distance of travel of the at least one directional guide. The at least one shuttle may comprise a series of locating features spaced according to the discrete increments of fine adjustments along the set distance of travel of the at least one directional guide. The at least one releasable lock may incorporate a detent which interfaces with the locating features incorporated in the at least one shuttle. The detent of the at least one releasable lock inhibits the movement of the at least one shuttle when the at least one releasable lock is in the first engaged configuration and does not inhibit movement of the at least one shuttle when the at least one releasable lock is in the second disengaged configuration.

The knee support may be configured such that at least one of the gross position, or the fine position adjustment is individually adjustable for each knee of the patient. The knee support may further comprise at least one visual indicator for the fine adjustment position of the knee support. The visual indicator may be configured to be readable in the first orientation and in the second orientation.

Also provided is a method for configuring a support apparatus configured to support the lower extremities of a patient. The method comprises the following steps:

placing locators of at least one bottom portion of at least one support apparatus onto indexing structures of a patient table of an imaging or treatment modality to select the gross position of the support apparatus;

positioning the patient on the support apparatus;

disengaging at least one releasable lock on the support apparatus;

slidably adjusting the support apparatus along a direction defined by at least one directional guide of the at least one support apparatus to a desired discrete position along the set distance of travel of the directional guide;

reengaging the at least one releasable lock on the support apparatus.

The method may further comprise the steps of:

selecting an orientation for a base portion of the at least one support apparatus;

placing at least one top portion configured to support the patient's anatomy onto the base portion of the at least one support apparatus;

positioning the patient on the support system.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. It is emphasized that according to common practice, the various features of the drawings may not be drawn to scale unless otherwise indicated. On the contrary, the dimensions of the various features may be expanded or reduced for clarity. Included in the drawings are the following figures.

DETAILED DESCRIPTION OF THE INVENTION

Figure 1:
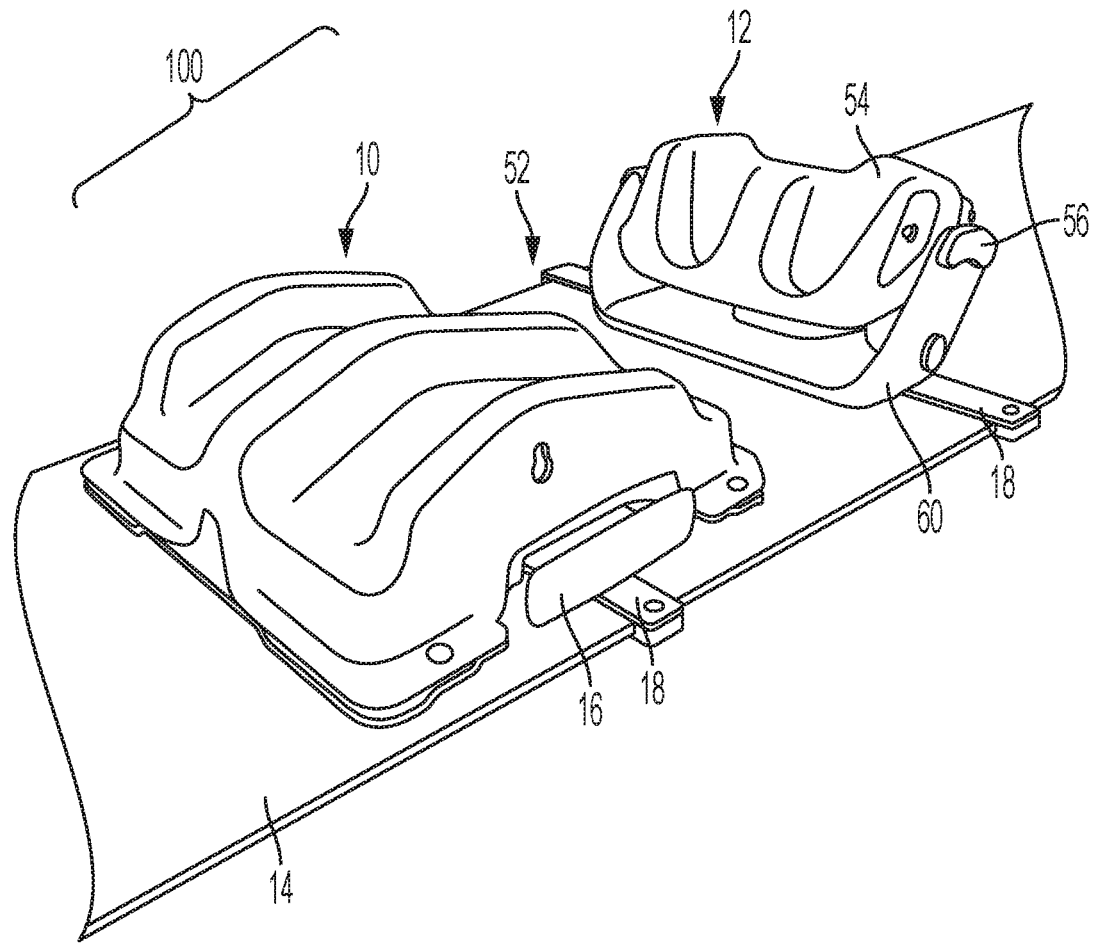
FIG. 1 shows a perspective view of an embodiment of the invention.

Although the invention is illustrated and described herein with reference to specific embodiments, the invention is not intended to be limited to the details shown. Rather, various modifications may be made in the details within the scope and range of equivalents of the claims and without departing from the invention.

Treatment of a patient undergoing radiotherapy often involves precise imaging and treatment procedures. Patients are typically imaged (or "simulated") on an imaging modality (including, but not limited to, X-ray, computed tomography (CT), magnetic resonance imaging (MRI), and positron emission tomography (PET)) to aid the clinician in determining appropriate treatment plans. Patients will then undergo treatment on a radiotherapy modality (including, but not limited to, linear accelerator (Linac), proton therapy, heavy ion therapy, and photon therapy). In some instances, the imaging and treatment modalities may be combined into one unit, as in commercially available combination MR imaging/linear accelerator systems (MR-Linac), which combine a magnetic resonance imaging system with an on-board linear accelerator to deliver treatment.

Regardless of the chosen imaging and/or treatment modalities, it is critical that the patient is positioned in the same position for treatment as they were initially imaged, as margins and dosages of radiation to the tumor or other target pathologies are determined based on the images obtained in simulation, with an eye to destroy the tumor or other target pathology while limiting incidental damage to healthy tissues as a result of treatment. Also key to smooth, accurate simulation and treatment, is patient comfort, as a patient who is uncomfortable may not be able to tolerate a particular position for the duration of a scan or treatment and may, as a result, inadvertently shift their position in a manner that is detrimental to the treatment plan.

In radiotherapy procedures like stereotactic body radiation therapy (SBRT) and in imaging procedures used in connection with radiotherapy, like computed tomography (CT) and magnetic resonance imaging (MRI), it is common to provide positioning and immobilization for patient comfort and repeatable positioning. Positioning and immobilization devices are often designed to accommodate particular areas of anatomy, including support of the lower extremities, which may be used independently or in conjunction with positioning devices for other areas of the body.

In particular, in radiotherapy, patients often require multiple treatment sessions over a period of weeks. It is required that the patient is set up in the same position from one session to the next. For this reason, discrete locations of the positioning devices are necessary. To ensure consistency and repeatability of imaging and treatment setups, devices typically need to be positioned or indexed to discrete locations on the patient table of the particular treatment or imaging modality. As there exists a great deal of variation in sizes and proportions of patient anatomy, patient range of motion, and patient comfort preferences, particularly as it relates to large regions of anatomy such as the lower extremities, it is desirable to allow for adjustment of any positioning devices once the patient is on the table. Exemplary currently available devices generally primarily accommodate gross adjustability along the superior to inferior axis of the patient table by mating to the provided locations of the indexing features provided on the patient table. While this broadly accommodates a range of patients, if an adjustment is deemed appropriate, these devices need to be lifted on and off a series of indexing features in order to be repositioned along the superior-inferior axis of the patient table. This is cumbersome, as it is often a challenge for the clinician to see the mating indexing features on the underside of the positioning device. Further, in these instances, the patient's anatomy may need to be lifted or otherwise moved from the device; for larger anatomical regions such as the lower extremities or for patients with limited strength or mobility to assist in these adjustments, the clinician may face additional difficulty with manipulating the patient anatomy, requiring significant time to reposition the patient afterwards and determine if further adjustments are necessary, severely impacting workflow efficiency as a result. Furthermore, due to the limitations of the discrete locations of indexing features, fine adjustments to positions within said discrete locations are not possible to effect with the systems of the prior art. Accordingly there is a need for patient positioning aids or supports where large manipulations of patient anatomy are limited and finer adjustments to positioning are accommodated, thereby enhancing clinical workflows and patient comfort.

The various aspects of the present invention disclosed herein alleviate these issues by introducing features for fine adjustments along a direction of the table which may be used while minimizing large manipulations of the patient's anatomy. The support apparatus and system of the present invention may further include features for adjustment of height and/or angular adjustment of the target anatomy to ensure optimal patient position for the particular clinical needs of the patient's treatment. As the various aspects of the present invention require minimal patient movement during adjustment, they enhance patient comfort, patient position reproducibility, and workflow efficiency.

There are several aspects to the present invention: support apparatus and system configured to support the anatomy of a patient, for example during radiotherapy and imaging procedures, and methods for employing the same.

Turning now to the figures, FIG. 1 shows a perspective view of an embodiment 100 of the support apparatus configured to support a patient's anatomy. As shown in FIG. 1, the support apparatus 100 includes the following components.

At least one support is configured to support a patient's anatomy. As shown in FIG. 1, two such supports are shown; a knee support 10 and a foot support 12. Each of the supports 10, 12 includes at least one respective locator (not visible in the FIG. 1 view) configured to removably locate the support apparatus 100 to a patient table 14 of a target modality (not shown).

The at least one knee support 10, and the at least one foot support 12, define an area 52, configured to accommodate lower portions of the patient's legs and feet, respectively. Also included in the support apparatus 100 is at least one directional guide (not visible in FIG. 1) having a set distance of travel.

The support apparatus 100 includes at least one shuttle (not visible in the FIG. 1 view) coupled to the support 10. The shuttle 36 is configured to slidably adjust the support along the directional guide in the superior/inferior direction.

The support apparatus 100 includes at least one releasable lock 16. The lock 16 is configured to restrict movement of the at least one shuttle along the directional guide in a first engaged configuration. The releasable lock 16 is also configured to enable movement of the shuttle along the directional guide (not visible in the FIG. 1 view) in a second disengaged configuration.

In use, a gross position of the support apparatus is selected by locating the locator to a corresponding structure 18 on the patient table 14 of the target modality. The corresponding structure 18 on the patient table 14 may be, for example, a two pin locating bar, as shown in FIG. 1. Once the gross position is set in this manner, the position of the support apparatus 100 may be further finely adjusted as will be described in more detail in the following discussion.

Figure 2:
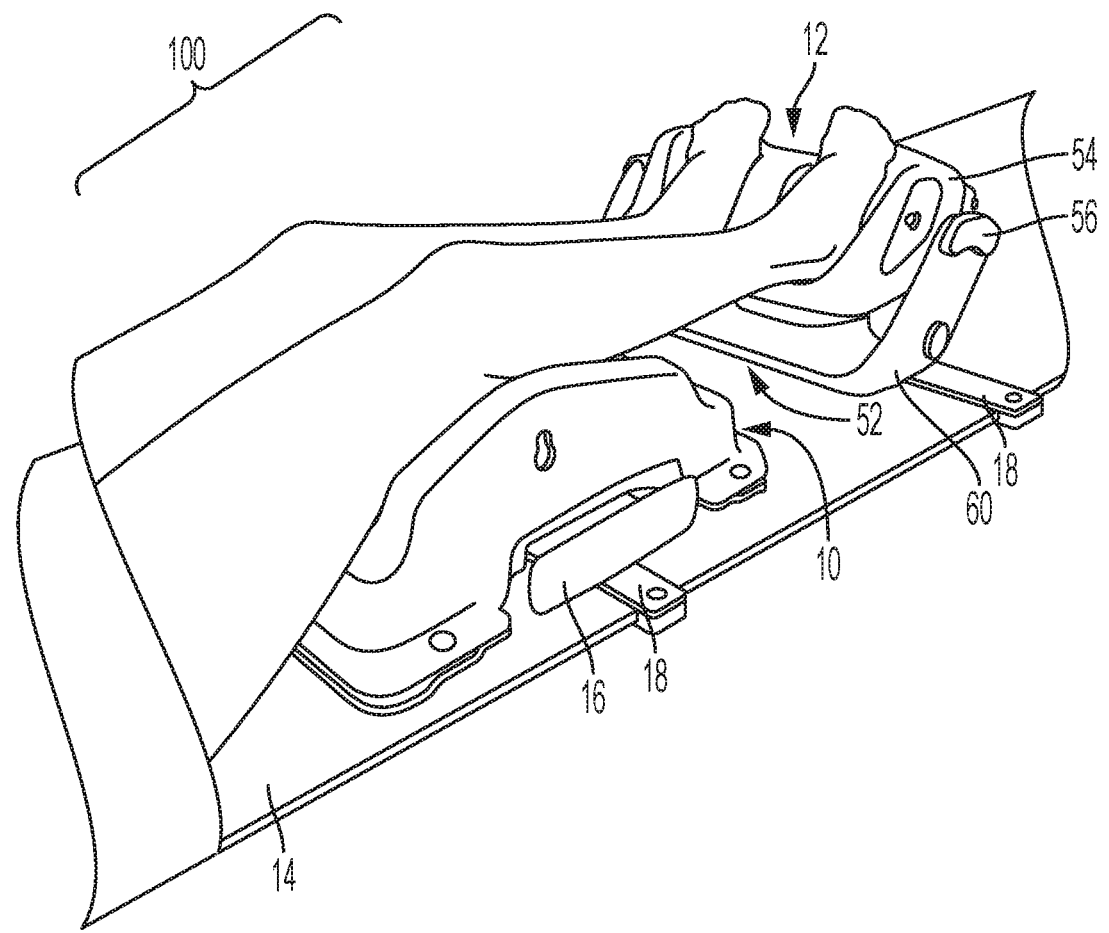
FIG. 2 shows another view of an embodiment of the invention in use.

The support apparatus 100 is capable of being finely adjusted in the superior/inferior direction with minimal manipulation of the patient's anatomy, while the patient is in position on the support apparatus. FIG. 2 is a view of the support apparatus 100 showing a patient's legs and feet in position on the knee support 10 and the foot support 12. The superior/inferior fine adjustment of the support apparatus 100 may be performed while the patient is positioned on the support apparatus 100. FIG. 2 also shows how the at least one knee support 10 and the at least one foot support 12 define an area 52 configured to accommodate lower portions of the patient's legs.

FIG. 1 shows that the foot support apparatus 12 also includes at least one tilting portion 54, including the at least one support, and wherein the at least one foot support 12, is further configured to be disposed at different discrete angles along a range, and comprises a lock 56, configured to secure the at least one tilting portion 54, at a desired discrete angle. At least one base portion 60 is coupled to the at least one tilting portion 54, and is additionally coupled to the at least one directional guide 34, the at least one locator 42, the at least one shuttle 36, and the at least one releasable lock 16.

Figure 3:
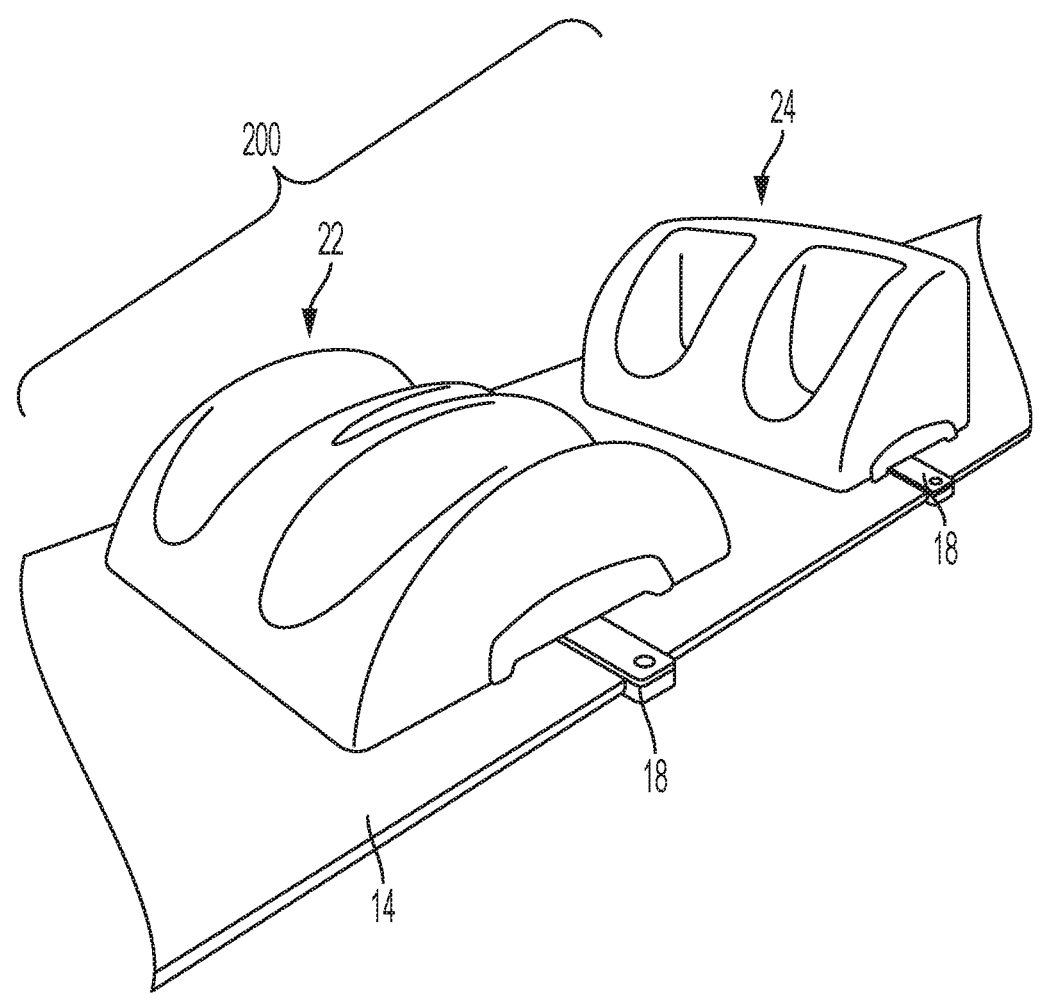
FIG. 3 shows a conventional apparatus.

By comparison, FIG. 3 shows an example of a conventional support apparatus 22 including a conventional knee support 22 and a conventional foot support 24, which are not capable of fine adjustment when a patient is in place on the conventional support apparatus 200. In the case of this conventional support apparatus 200, the knee support 22 and the foot support 24 each may include locators on their respective undersides (not shown in FIG. 3.) that are configured to attach to the corresponding structure 18, such as a 2-pin locating bar, on the patient table 14. As is known in the art, attaching the knee support 22 and the foot support 24 to the locator bar 18 on the patient table 14 is the only possible adjustment for the conventional support apparatus 200.

Figure 4:
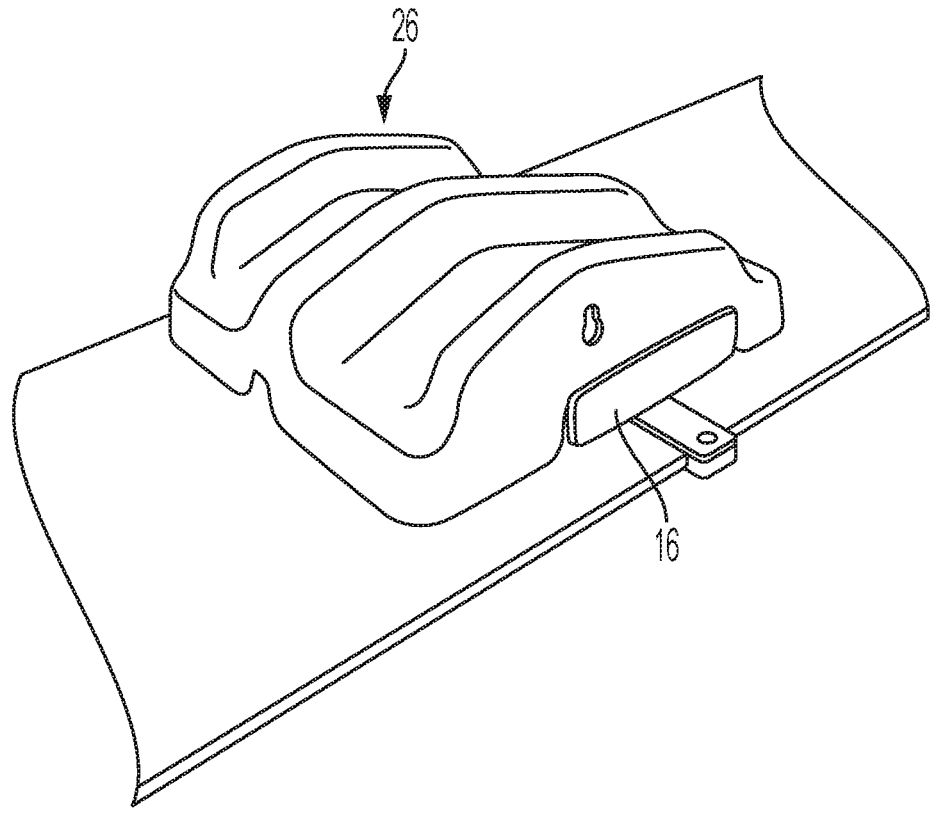
FIG. 4 shows another embodiment of the invention.

FIG. 4 shows another embodiment of a knee support 26. This knee support 26 is capable of fine adjustment in the superior/inferior direction while the patient is in place on the support 26, since this embodiment also includes a releasable lock 16.

Figure 5:
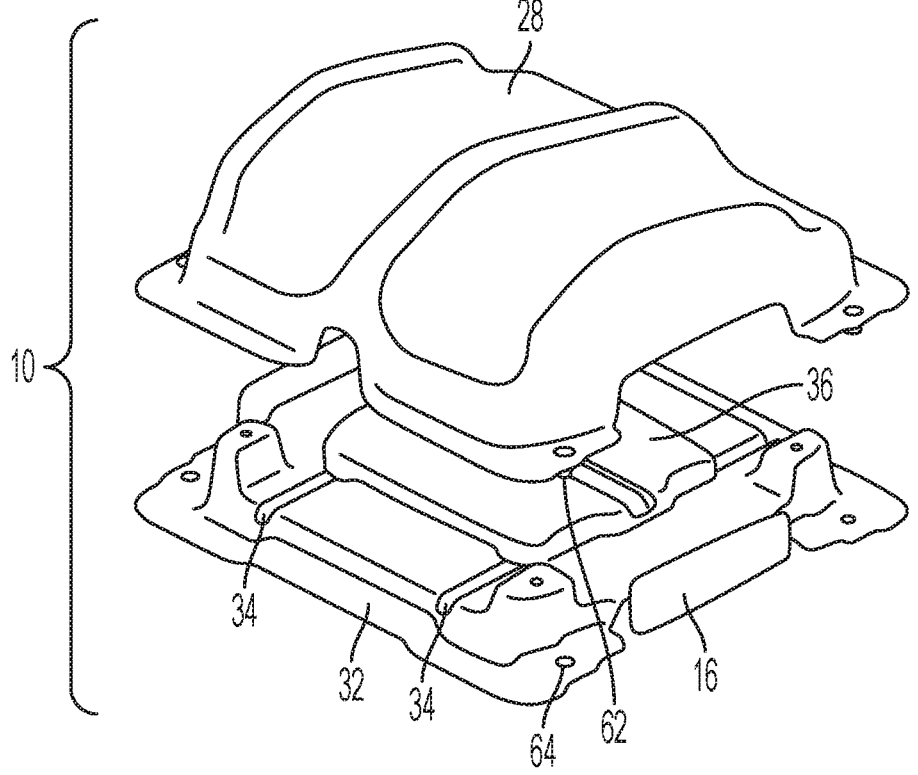
FIG. 5 shows an exploded view of an embodiment of the invention.

Turning now to FIGS. 5-11, the fine adjustment will be described and explained. FIG. 5 shows an exploded version of the support structure 10 intended for knee support. The following description is with respect to this knee support structure 10, but a person skilled in the art would understand that the principles and components as described herein will also apply to a support structure intended to support a patient's feet, i.e. foot support 12 (not shown in FIG. 5).

As shown in FIG. 5, the support structure 10 includes a top portion 28 and base portion 32. The top portion 28 is configured to support a patient's legs at an area around their popliteal fossa. The base portion 32, is removably attached to the top portion 28. As can be seen in FIG. 5, the base portion 32 includes directional guides 34. As shown in FIG. 5, these directional guides 34 may optionally be directly molded in the base portion 32. The directional guides 34 provide a set distance and direction of travel. Non-limiting examples of other types of such directional guides 34 include a track, a rail, a rack, or a slot.

Figure 6A:
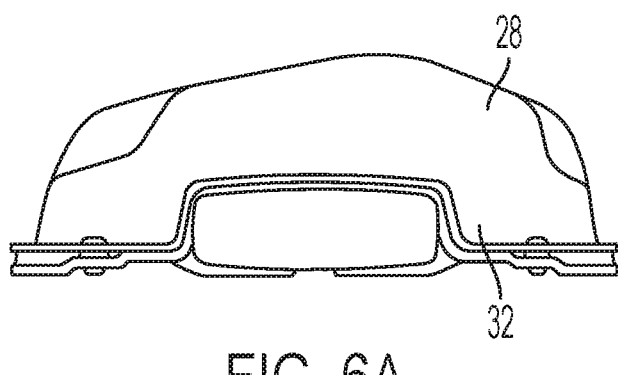
FIGS. 6A, 6B, and 6C show an exemplary embodiment of the invention.
Figure 6B:
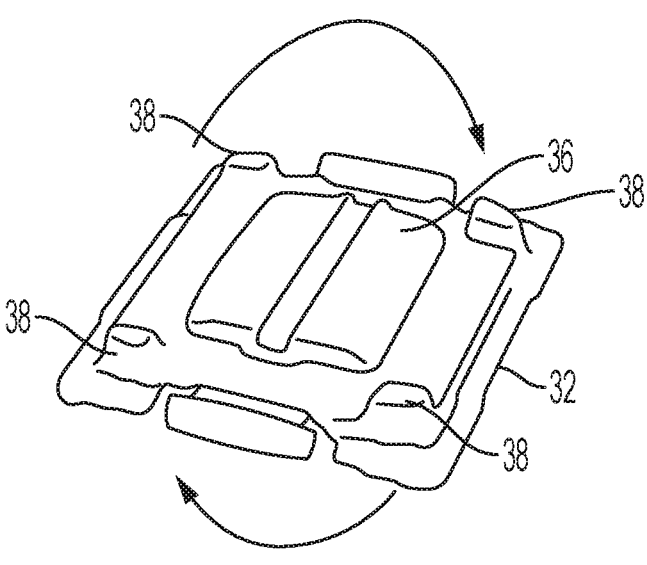
Figure 6C:
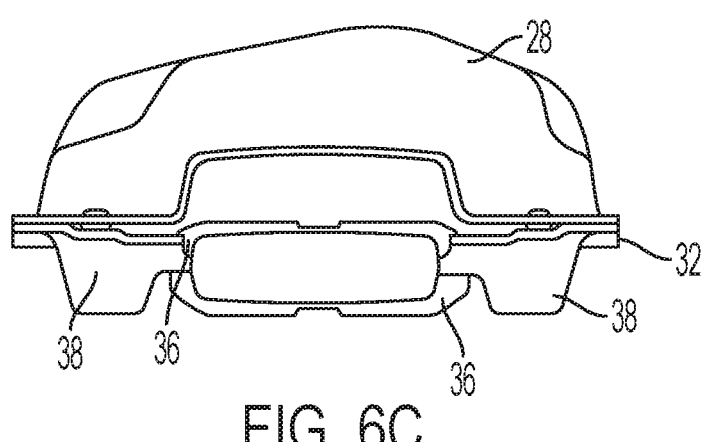

As discussed above, the support apparatus 100 includes at least one shuttle 36. The embodiment shown in FIG. 5 has two such shuttles 36 on the foot support structure 12 of the support apparatus, although only one is visible. The other shuttle is on the opposing side of the base portion 32 from the side that is visible in FIG. 5. FIGS. 6A, 6B and 6C show how an embodiment of the base portion 32 may be two-sided and thus include two such shuttles 36 or have a dual-sided shuttle 36.

This embodiment of the base portion is therefore "flippable" as indicated by the arrows in FIG. 6B. These two possible orientations of the base portion 28 are shown in FIGS. 6A and 6C, respectively. As may been seen in FIGS. 5 and 6, the base portion 32 includes feet 38. In the orientation of FIG. 6A, the feet 38 are oriented away from the patient support table 14 (not shown), so that the top portion 28 is lower in height or elevation. When the base position 32 is flipped over (FIG. 6B), the feet 38 are oriented towards the patient table 14 and thus the top portion is at a higher elevation. Thus, by flipping the base portion 32, the height of the support structure 12 may be adjusted. In FIG. 6, it should also be appreciated that one of the two shuttles 36 is always facing the patient table 14 (not shown).

Figures 7A, 7B:
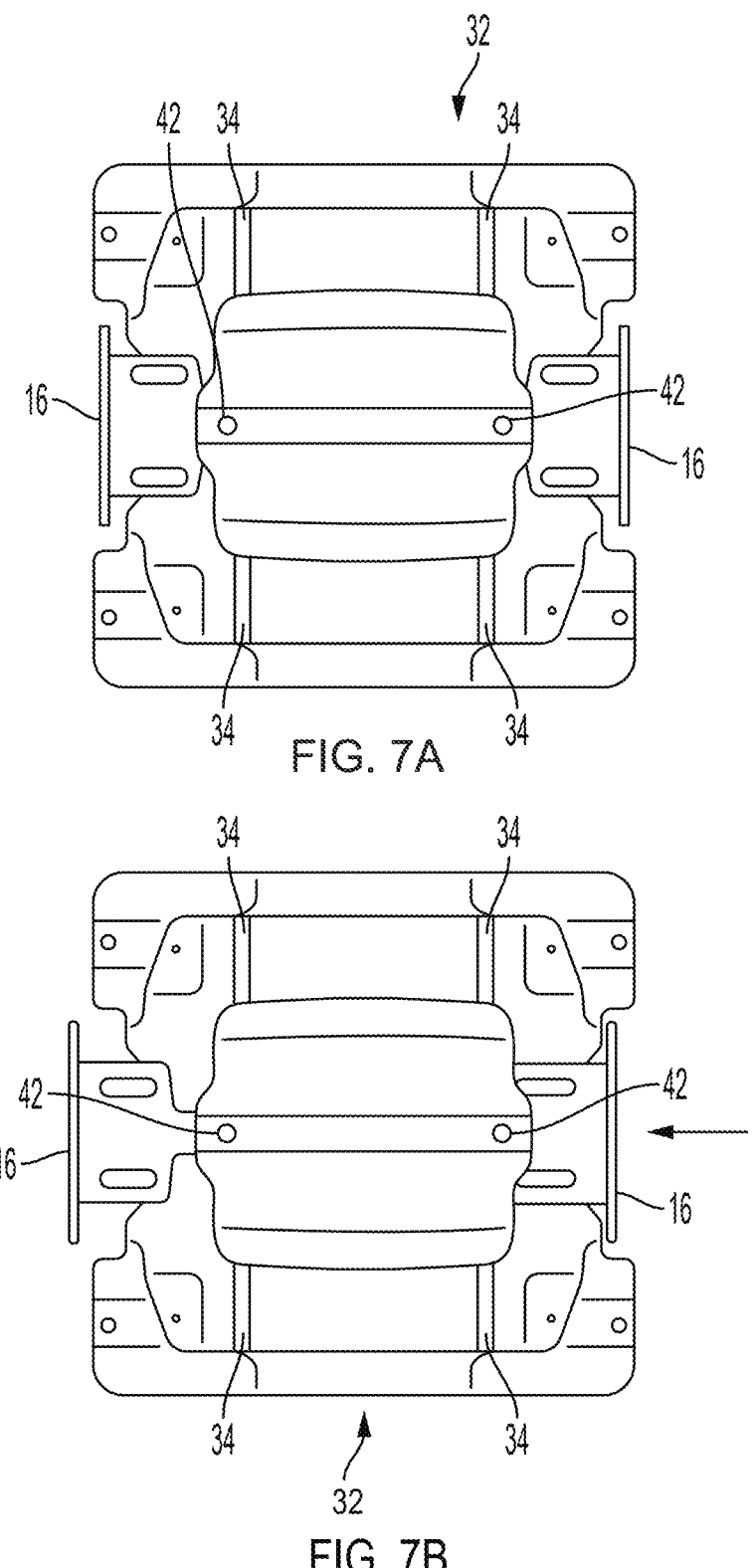
FIGS. 7A and 7B show different configurations of an embodiment of the invention.

Turning next to FIGS. 7A and 7B, the side of the base portion 32 facing the patient table 14 (not shown) is seen. The shuttles 36 include locators 42 which are configured to removably locate the support 12 with respect to the patient table 14 (FIG. 1) of a target modality (not shown). According to embodiments, the at least one locator 42 may be configured to receive at least one pin or at least one disc located on the target modality. For example, the locator 42 may be an aperture that is configured to receive a pin on a two-pin locating bar. Alternatively, for example, the locator 42 may be a pin that is configured to be received into an aperture on a locating bar on the patient table of a target modality.

FIGS. 7A and 7B also show movement of the releasable lock 16, which effects the fine adjustment of the support 10 with respect to the patient table 14. As shown in FIG. 7A, the releasable lock 16 is in the first engaged configuration, where the base portion 32 is not able to slide with respect to the shuttle 16. Since, as described above, the shuttle 16 is held in place in a gross position with respect to the patient table 14, the entire support structure 12 is likewise held in position. As shown in FIG. 7B by the arrow, the releasable lock 16 may be pushed sideways, thus allowing the base portion 32 to slide in the inferior/superior direction along the directional guides 34 with respect to the shuttle 36, since the shuttle 36 is held the gross position with respect to the patient table 14.

Figure 8:
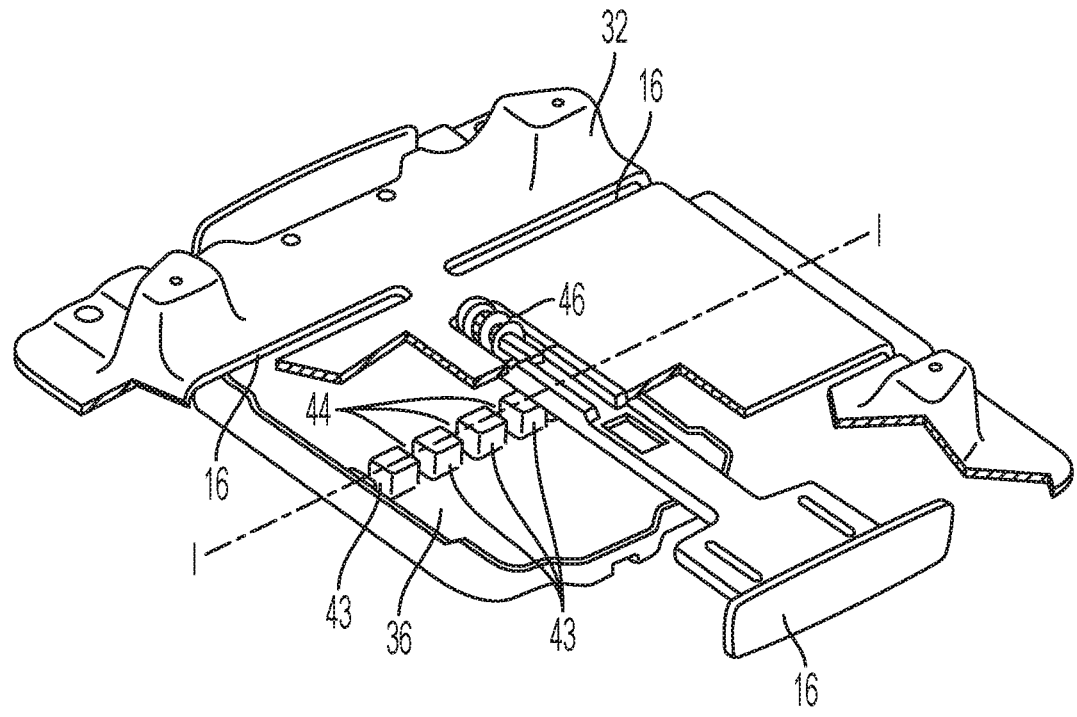
FIG. 8 shows a partial cutaway of an embodiment of the invention.

FIG. 8 shows in partial cutaway, the base portion 32, the releasable lock 16, and the shuttle 36. It should be understood that, in this embodiment, these components have bilateral symmetry along the line I-I in FIG. 8. As can be seen in FIG. 8, the shuttle 36 incorporates a series of locating features 43. As shown in FIG. 8, an exemplary embodiment of these locating features 43 is a series of projections that define a series of notches 44 therebetween. These locating features 43 are spaced so as to provide discrete increments of fine adjustments along the set distance of travel along the directional guides 34.

Also shown in FIG. 8. is a biasing element or a tensioner. In the embodiment shown in FIG. 8, this tensioner is in the form of a spring 46. Other non-limiting examples of suitable tensioners are an elastic band or a belt. More than one such tensioner type may be utilized or different types of tensioners may be present in the same support apparatus. This may also be accomplished with a compressible member or structure. The spring 46 is configured and arranged to return the releasable lock 16 to its first engaged position from the second disengaged position.

Figures 9A, 9B, 9C, 9D:
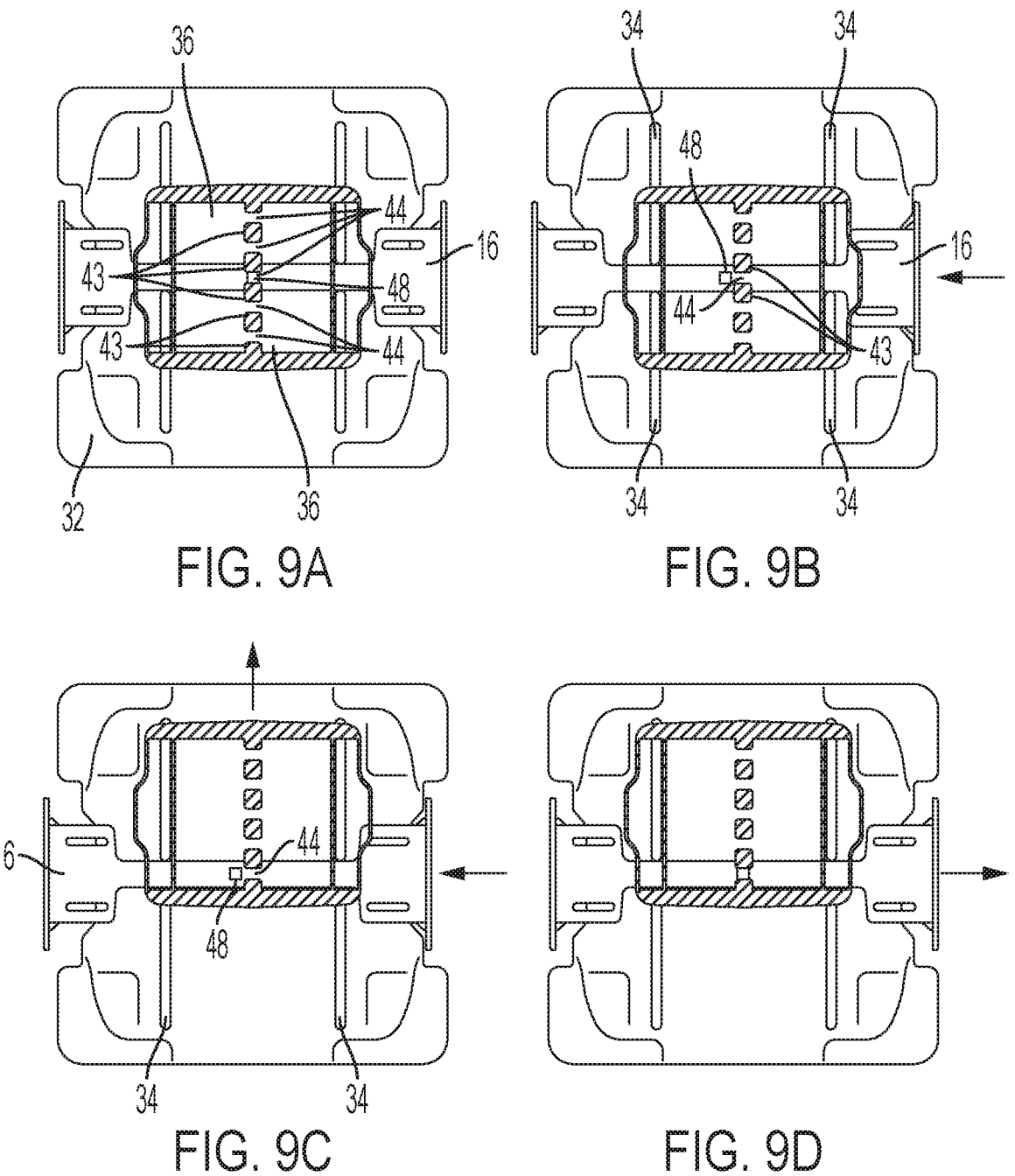
FIGS. 9A, 9B, 9C and 9D show various configurations of an embodiment of the invention.

Turning next to FIGS. 9A-9D, the operation of the fine adjustment is shown in more detail. In FIGS. 9A-9D, the shuttle 36 is shown in cross section. In FIG. 9A, the releasable lock 16 is in the first engaged configuration. In this engaged configuration, a detent 48 (also referred to herein as a tooth) located on the releasable lock 16 is engaged in, or interfaces with one of the notches 44 located between two adjacent locating features 43.

Since the springs 46 (not visible) are configured to hold the releasable lock 16 in this first engaged configuration, the base portion 32 and thus the support structure 10 or 12 will be held in position on the patient table 14 of the target modality. Thus movement of the support structure 10 or 12 with respect to the patient table 14 is inhibited. To release the releasable lock 16, it may be pushed or pulled against the bias of the tensioner in the direction shown by the arrow in FIG. 9B. This push or pull force disengages the detent 48 from the notch 44.

As shown in FIG. 9C, the releasable lock is now is the second disengaged configuration and the base portion 32 may then be slidably adjusted with respect to the shuttle 36 along the directional guides 34 as shown by the arrow in FIG. 9C. Finally, in FIG. 9D, the push or pull force on the releasable lock 16 is removed and thus the tensioner urges the releasable lock 16 back to the first engaged configuration. However, as may be appreciated by comparing FIG. 9A with FIG. 9D, the base 32 (and thus the entire support structure) is finely adjusted to a different fine position. This fine adjustment may thus be seen as enabling smaller increments of movement than is possible by utilizing only the locator 42 and the corresponding structure 18.

As may be seen in FIGS. 9A-9D, the locating features 43 and notches 44 are located at discrete increments along the set distance of travel of the at least one directional guide 34. Any reasonable number of these locating features 43 and corresponding notches may be utilized, e.g., 3 locating features and 2 notches, 5 locating features and 4 notches, 4 locating features and 3 notches, or 6 locating features and 5 notches, etc. It will appreciated by a person having skill in the art that these projections 43 and notches 44 are not the only geometry possible. For example, a series of apertures may serve the same purpose.

Figures 10A, 10B:
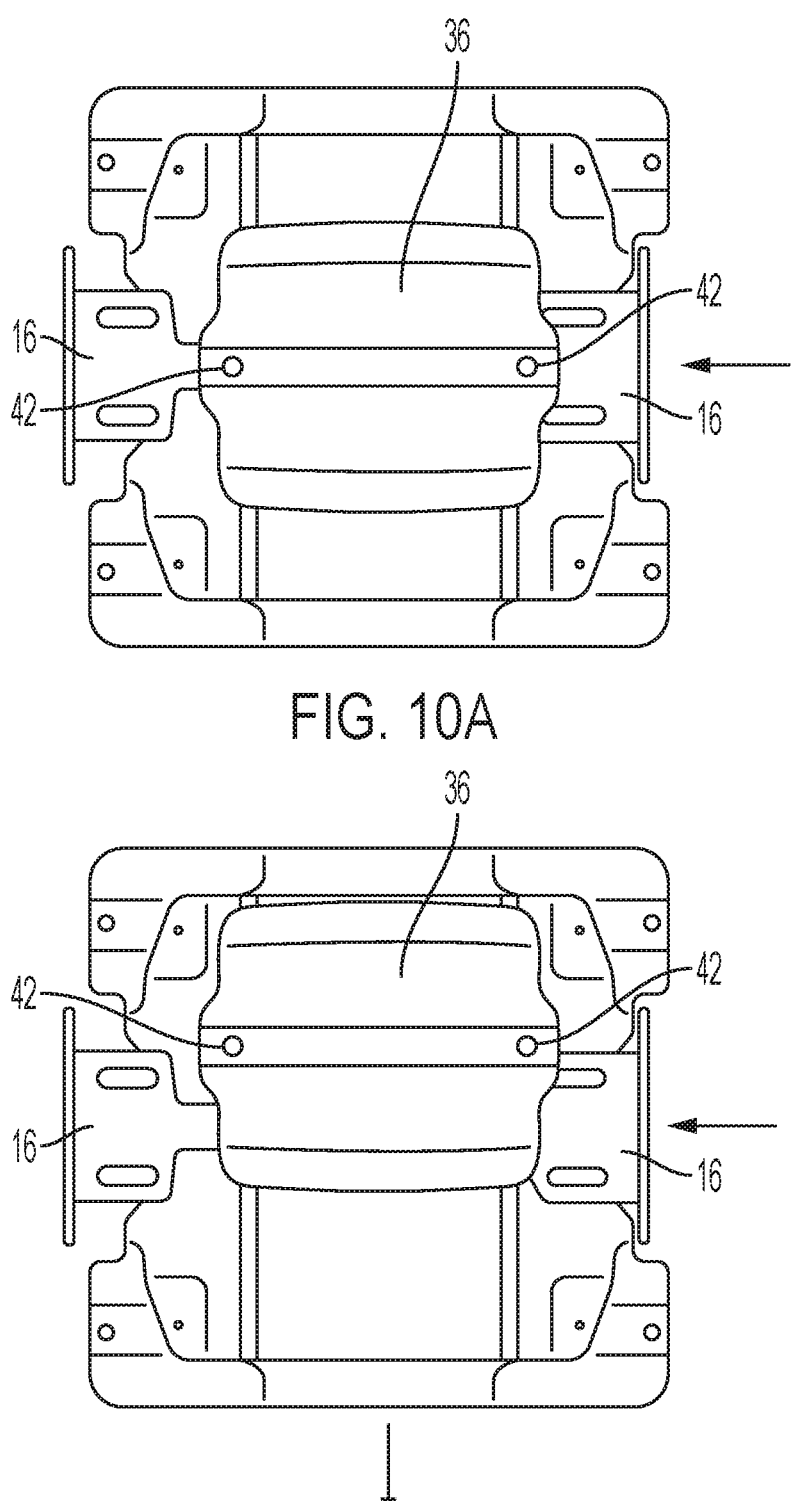
FIGS. 10A and 10B show various configurations of an embodiment of the invention.

FIGS. 10A and 10B show another view of the fine adjustment capability of the shuttle 36, but unlike FIGS. 9A-9D, FIGS. 10A and 10B are not in cross section. In FIG. 10, the locators 42 that are configured to accept the corresponding structure, such as pins on a two-pin locator bar, are visible. FIG. 10A shows the releasable lock 16 in the first engaged configuration and FIG. 10B shows releasable lock 16 in the second disengaged configuration.

Figure 11:
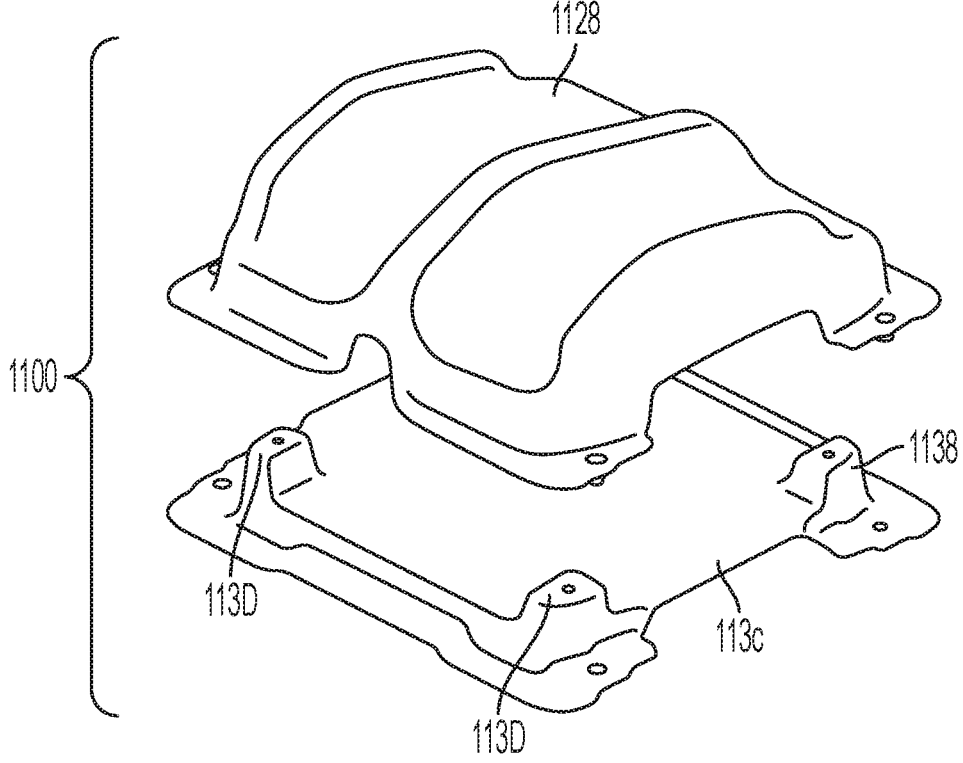
FIG. 11 shows an exploded view of an embodiment of the invention.

FIG. 11 shows an exploded version of another embodiment of a support structure 1100 for the knees of a patient. In this embodiment, the support structure 1100 has a top portion 1128 and a base portion 1132, but does not incorporate the releasable lock. In this embodiment 1100, the base portion 1132 is flippable, as shown in FIG. 6. Thus, the base portion incorporates feet 1138. As shown in FIG. 11, the feet 1138 are directed towards the top portion 1128 and therefore the support 1100 has a reduced height or elevation compared to a configuration (not shown) where the feet 1138 are directed away from the top portion 1128.

Figure 12:
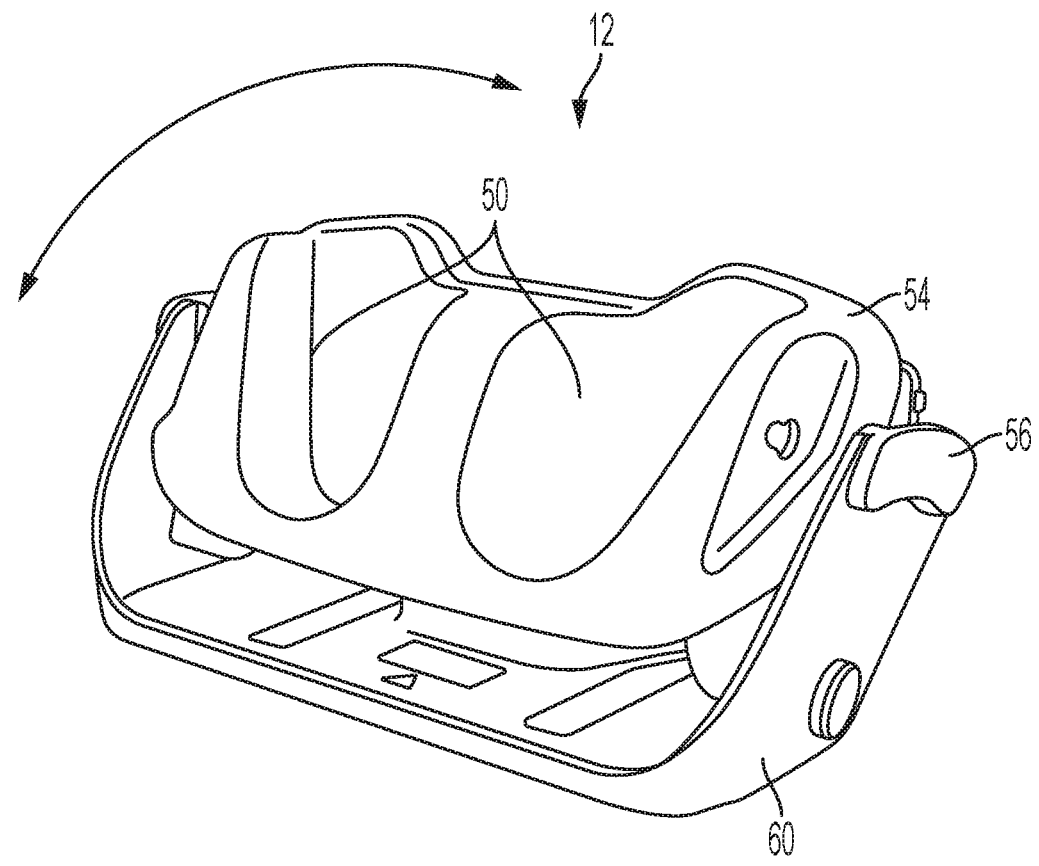
FIG. 12 shows an embodiment of the invention.

FIG. 12 shows a view of a support structure 12 that is configured to support the feet of a patient. As shown in FIG. 12, by the arrow, this foot support structure 12 is configured to move in a tilting motion. The foot support 12 is configured to support the soles and heels of the patient's feet. As may be seen in FIG. 12, in this embodiment, the soles and heels may be supported in the depressions 50. When the foot support 12 is tilted, the angle of the patient's feet may be adjusted.

Figure 13:
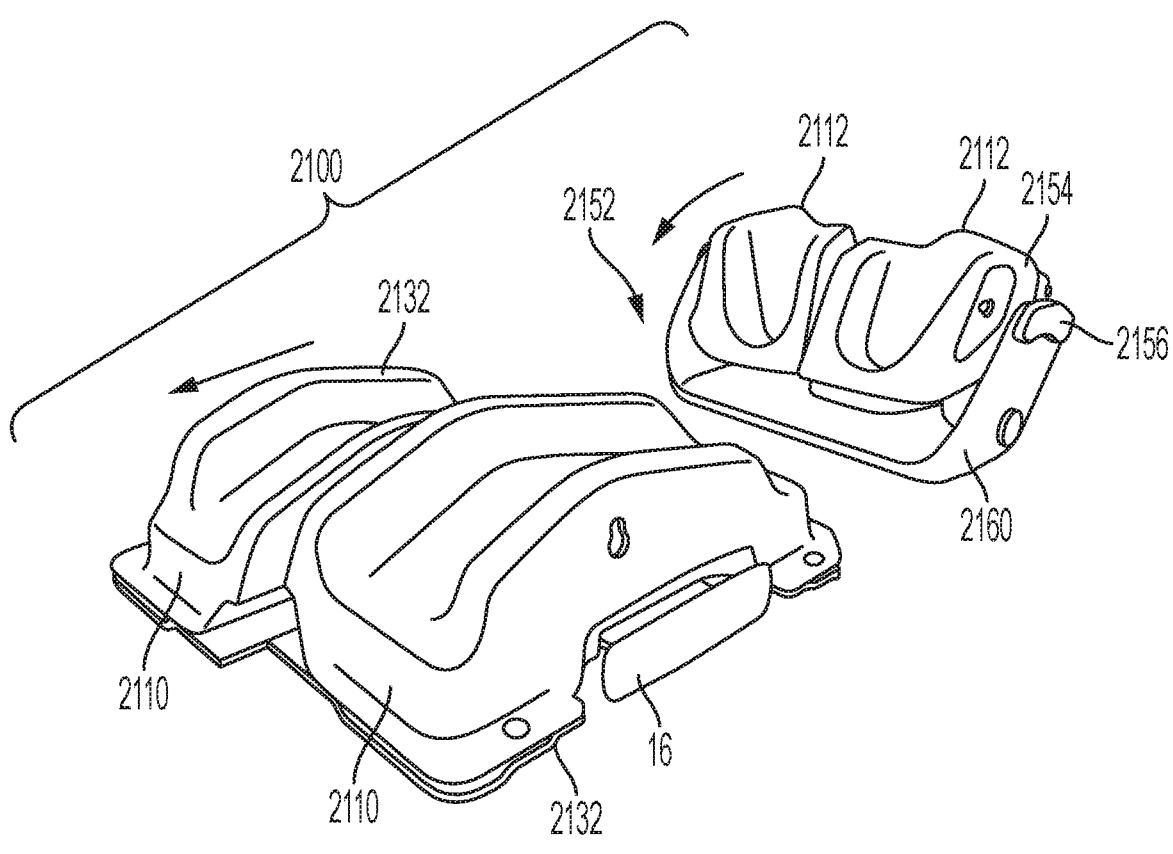
FIG. 13 shows a view of an embodiment of the invention.

FIG. 13 shows a perspective view of another embodiment 2100 of the support apparatus configured to support a patient's anatomy. As shown in FIG. 13, the support apparatus 2100 includes the following components.

At least one support is configured to support a patient's anatomy. As shown in FIG. 13, four such supports are shown; two knee supports 2110 and two foot supports 2112. The at least one knee support 2110 and the at least one foot support 2112 define an area 2152 configured to accommodate lower portions of the patient's legs. Each of the supports 2110, 2112 includes at least one respective locator (not visible in the FIG. 13 view) configured to removably locate the support apparatus 2100 to a patient table of a target modality (not shown).

Also included in the support apparatus 2100 is at least one directional guide (not visible in FIG. 13) having a set distance of travel. The support apparatus 2100 includes at least one shuttle (not visible in the FIG. 1 view) coupled to the supports 2110 and 2112. The shuttle is configured to slidably adjust the support along the directional guide in the superior/inferior direction.

The support apparatus 2100 includes releasable locks 16 on each support structure 2110, 2112. As described above, the locks 16 are configured to restrict movement of the at least one shuttle along the directional guide in a first engaged configuration. The releasable lock 16 is also configured to enable movement of the shuttle along the directional guide (not visible in the FIG. 13 view) in a second disengaged configuration.

In use, a gross position of the support apparatus is selected by locating the locator to a corresponding structure on the patient table of the target modality. The corresponding structure on the patient table may be for example, a two-pin locating bar. Once the gross position is set in this manner, the position of the support apparatus 2100 may be further finely adjusted as is described in more detail above. The support apparatus 2100 is capable of being finely adjusted in the superior/inferior direction with minimal manipulation of the patient's anatomy, while the patient is in position on the support apparatus. It also permits separate and independent adjustment of the patient's legs and/or feet.

The internal mechanism of the support apparatus 2100 corresponds to is that of prior embodiments but is duplicated for each of the separately movable knee and foot supports. For example, FIGS. 8-10 thus show the detent 43 of the at least one releasable lock 16 inhibits movement of the at least one shuttle 36 when the at least one releasable lock 16 is in the first engaged configuration and does not inhibit movement of the at least one shuttle 36 when the at least one releasable lock 16 is in the second disengaged configuration. These FIGS. 8-10 also show that the at least one releasable lock 16 further comprises at least one tensioner 46 configured to return the at least one releasable lock 16 to the first engaged configuration from the second disengaged configuration. As discussed above, the at least one tensioner 46 may be selected from the group consisting of a spring, an elastic band a belt, and combinations thereof, or may be a compressible member or other biasing element FIG. 14 shows the knee support further comprising at least one visual indicator for the fine adjustment position of the knee support, wherein the visual indicator is configured to be readable in the first orientation and in the second orientation.

The at least one support structure 10, 12, 2112, 2110 may be constructed of a rigid material. In another embodiment, the at least one support structure 10, 12, 2112, 2110 may be constructed of a deformable material configured to conform to a patient's anatomy. In an embodiment, the components of the support apparatus 100, 2100 may be composed of materials which are compatible with a magnetic resonance imaging (MRI) environment.

As discussed above, the support apparatus 2100, 100 may be additionally capable of height adjustment. In an embodiment, the support apparatus 2100, 100 may additionally be capable of adjusting an angle of a patient's anatomy. This is shown in FIG. 12 and FIG. 13, where the arrows show how the foot support 12, 2112 may be tilted. As may be seen in FIG. 12, in this embodiment, the soles and heels may be supported in the depressions 50. When the foot supports 12 or 2112 are tilted, the angle of the patient's feet may be adjusted.

Figure 14A:
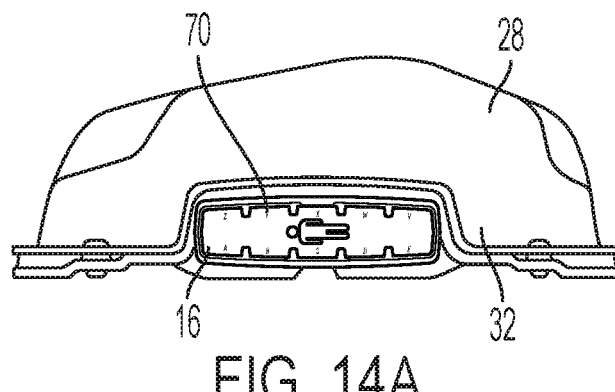
FIGS. 14A, B, and C show an exemplary embodiment of the invention.

FIGS. 14A, B, and C show an embodiment of the knee support 10, that is similar to the embodiment shown in FIGS. 6A-6C. This embodiment incorporates at least one visual indicator 70 for the fine adjustment position of the knee support 10. In the embodiment shown, the visual indicator 70 is in the form of a label that may be attached to the releasable lock 16. This embodiment has the "flippable" base portion 32 as is indicated by the arrows in FIG. 14B. These two possible orientations of the base portion 28 are shown in FIGS. 14A and 14C, respectively. As may been seen in FIG. 5 and 6, the base portion 32 includes feet 38. In the orientation of FIG. 14A, the feet 38 are oriented away from the patient support table 14 (not shown), so that the top portion 28 is lower in height or elevation. When the base position 32 is flipped over (FIG. 6B), the feet 38 are oriented towards the patient table 14 and thus the top portion is at a higher elevation. Thus, by flipping the base portion 32, the height of the support structure 12 may be adjusted.

Figure 14B:
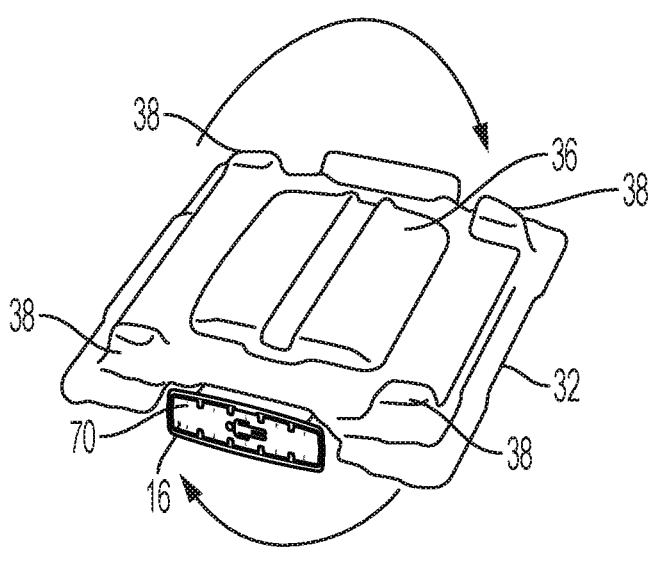
Figure 14C:
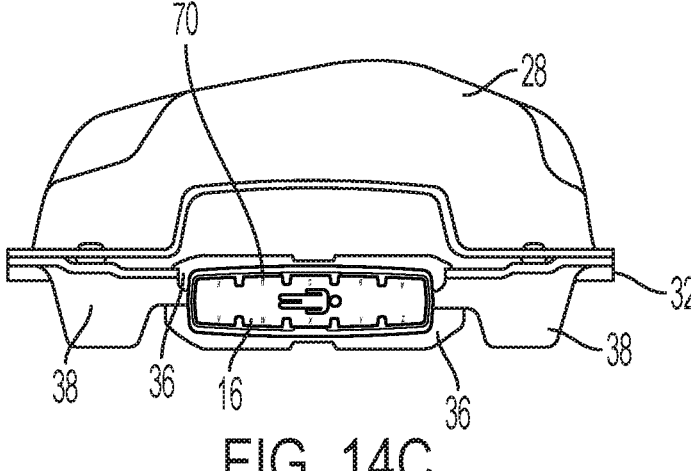
Figure 15:
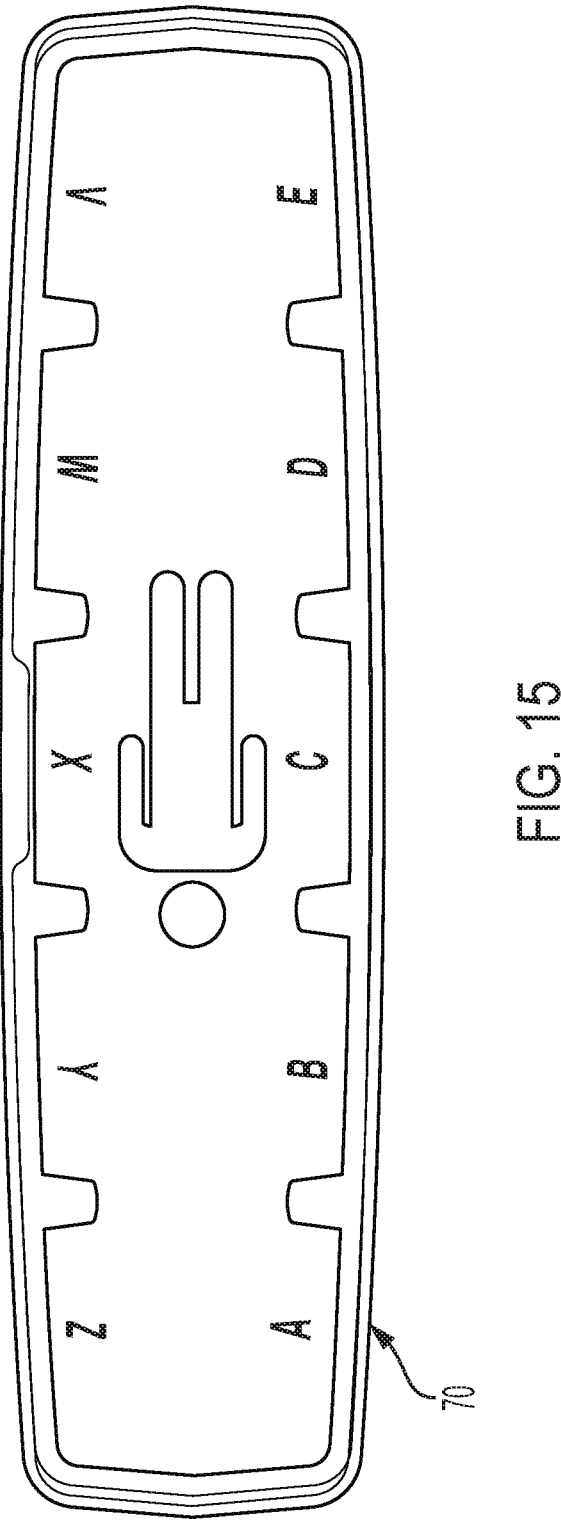
FIG. 15 shows an embodiment of the invention.

As can be seen in FIGS. 14A-14C, the visual indicator 70 is configured to be readable in the first orientation and in the second orientation. The letters A-E on one side of the outer edge and the letters V-Z on the opposite outer edge of the visual indicator 70 are spaced apart to correspond to the notches 44 between the locating features 43. When the knee support is flipped, as indicated by the arrows in FIG. 14B, and/or slidably adjusted in the fine adjustment in the superior/inferior directions, the letters will indicate that the apparatus is positioned in one of the discrete fine adjustment increments of the support apparatus. In an embodiment, these indicators may line up with a landmark (not shown) on the patient table of the modality or on the support apparatus itself, for example. A convenient example of such landmark is the corresponding structure 18 on the patient table of the modality or on the support apparatus. This provides a visual indication of the location of the knee support 10 with respect to the patient table of the modality in both its height and its superior/inferior direction. FIG. 15 shows a larger view of the visual indicator 70. Although not shown, a mirror image of this label may be affixed to the opposite side of the releasable lock 16 (not visible in FIG. 14.)

This visual indication makes it possible for the user of the apparatus to record the position (height and fine adjustment)

so that it can be easily reproduced for subsequent imaging or treatment of the same patient. The visual indicator also facilitates the efficient and accurate repositioning of the apparatus, thus saving time and effort while improving treatment accuracy and precision. Accordingly, the indicator 70 makes it easy for the user of the system to visualize, monitor, and record in notes the actual position, in terms of height and/or fine adjustment, of the apparatus.

As shown in FIGS. 1-14 a support system 100, 2112 configured to support the anatomy of a patient is provided. The support system 100, 2112 may comprise a plurality of support apparatus 10, 12, 2110, 2112. At least one of the support apparatus 10, 12, 2110, 2112 in the plurality may include the following components:

at least one support 10, 12, 2110, 2112 configured to support a patient's anatomy;

at least one locator 42 configured to removably locate the at least one support apparatus 10, 12, 2110, 2112 to a patient table 14 of a target modality;

at least one directional guide 34, the at least one directional guide 34 having a set distance of travel;

at least one shuttle 36 coupled to the at least one support 10, 12, 2110, 2112, configured to slidably adjust the at least one support 10, 12, 2110, 2112 along the at least one directional guide 34; and at least one releasable lock 16 configured to restrict the movement of the at least one shuttle 36 along the at least one directional guide 34 in a first engaged configuration, and enable movement of the at least one shuttle 36 along the at least one directional guide 34 in a second disengaged configuration.

As shown particularly at FIGS. 1, 2, and 4, a gross position of the at least one support apparatus 10, 12, 2110, 2112 is selected by locating the at least one locator 42 of each of the support apparatus 10, 12, 2110, 2112 in the plurality to a corresponding structure 18 on the patient table 14 of the target modality and a position of at least one of the support apparatus 10, 12, 2110, 2112 in said plurality may be further finely adjusted.

The position of the at least one of the support apparatus 10, 12, 2110, 2112 in the plurality of support apparatus is capable of being finely adjusted with minimal manipulation of the patient's anatomy. As disclosed herein, "minimal manipulation" is understood to mean that the leg and or foot of the patient may remain in place on the support apparatus 10, 12, 2110, 2112 while the fine adjustments as described above are performed.

According to embodiments, each one of the support apparatus in the plurality of support apparatus 10, 12, 2110, 2112 may comprise at least one directional guide 34, at least one shuttle 36, and at least one releasable lock 16 and thus each one of the support apparatus 10, 12, 2110, 2112 in the said plurality may be capable of being finely adjusted.

The at least one directional guide 34 of at least one of the support apparatus 10, 12, 2110, 2112 in the plurality of support apparatus may be selected from the group consisting of a track, a rail, a rack, a slot, and combinations thereof. The at least one locator 42 of the at least one support apparatus 10, 12, 2110, 2112 in the plurality of support apparatus is configured to receive at least one corresponding structure 18 located on the target modality. Non-limiting examples of such corresponding structures are a pin or at least one disc located on the target modality. The at least one locator of the at least one support apparatus 10, 12, 2110, 2112 in the plurality of support apparatus may be configured to receive pins of a conventional locating bar.

According to embodiments of the support system 100, 2100, the at least one of the support apparatus in the plurality of support apparatus 10, 12, 2110, 2112 may be finely adjusted in discrete increments along the set distance of travel of the at least one directional guide 34 of the at least one support apparatus 10, 12, 2110, 2112 in the plurality of support apparatus.

In an embodiment of the support system, at least one of the at least one support apparatus 10, 12, 2110, 2112 in the plurality of support apparatus may at least three discrete increments of fine adjustment. These discrete increments may be in the form of notches 44 in between projections or locating features 43 on the shuttle 36. The at least one shuttle 36 may comprises a series of locating features 43 that are spaced according to the discrete increments of fine adjustments along the set distance of travel of the at least one directional guide 34 of the at least one support apparatus 10, 12, 2110, 2112 in the plurality of support apparatus.

The at least one releasable lock 16 of the at least one support apparatus 10, 12, 2110, 2112 in the plurality of support apparatus may incorporate a detent 48, also referred to herein as a tooth which interfaces with the locating features 43 incorporated in the at least one shuttle 36 of the at least one support apparatus 10, 12, 2110, 2112 in the plurality of support apparatus. According to an embodiment, the detent 48 inhibits movement of the at least one shuttle 34 when the at least one releasable lock 16 is in the first engaged configuration and does not inhibit movement of the at least one shuttle 16 when the at least one releasable lock 16 is in the second disengaged configuration. The at least one releasable lock 16 further comprises at least one tensioner 46 configured to return the at least one releasable lock 16 to the first engaged configuration from the second disengaged configuration. The at least one tensioner 46 may be selected from the group consisting of a spring, an elastic band, a belt, and combinations thereof.

The at least one support 10, 12, 2110, 2112 may be constructed of a rigid material. The at least one support 10, 12, 2110, 2112 may be constructed of a deformable material configured to conform to the patient's anatomy. The components of the support system 100, 2100 may be composed of materials which are compatible with a magnetic resonance imaging (MRI) environment. In an embodiment the at least one of the support apparatus 10, 12, 2110, 2112 in the plurality of support apparatus may be additionally configured for at least one of height adjustment or angular adjustment. In an embodiment, each support apparatus 10, 12, 2110, 2112 in the plurality of support apparatus may be configured such that at least one of the gross position, fine position, height, or angle of each support apparatus is capable of being adjusted independently of the gross position, fine position adjustment, height, or angle of at least one other support apparatus in the plurality of support apparatus.

According to an embodiment, a support system 100, 2100 configured to support the legs of a patient is provided. The support system may comprise the following components:

at least one knee support 10, 2110 having:

at least one support 10, 2110 configured to support a patient's legs at an area around the popliteal fossa;

at least one locator 42 configured to removably locate the at least one knee support 10, 2110 to a patient table 14 of a target modality;

at least one directional guide 34 having a set distance of travel;

at least one shuttle 36 coupled to the at least one support 10, 2110, configured to slidably adjust the support 10, 2110 along the at least one directional guide 34; and at least one releasable lock 16 configured to restrict movement of the at least one shuttle 36 along the at least one directional guide 34 in a first engaged configuration, and enable movement of the at least one shuttle 36 along the at least one directional guide 34 in a second disengaged configuration; and at least one foot support 12, 2112 having:

at least one support 12, 2112 configured to support the soles and heels of the patient's feet;

at least one locator 42 configured to locate the at least one foot support 12, 2112 to a patient table 14 of a target modality;

at least one directional guide 34 having a set distance of travel;

at least one shuttle 36 coupled to the at least one support 12, 2112, configured to slidably adjust the support 12, 2110 along the at least one directional guide 34; and at least one releasable lock 16 configured to restrict movement of the at least one shuttle 36 along the at least one directional guide 34 in a first engaged configuration, and enable movement of the at least one shuttle 36 along the at least one directional guide 34 in a second disengaged configuration.

The at least one knee support 10, 2110 and the at least one foot support 12, 2112 define an area 52, 2152 configured to accommodate lower portions of the patient's legs. A gross position of each of the at least one knee support 10, 2110 and the at least one foot support 12, 2112 is selected by locating the at least one locator 42 of each of the at least one knee support 10, 2110 and the at least one foot support 12, 2112 to at least one corresponding structure 18 on the patient table 14 of the target modality and wherein a position of each of the at least one knee support 10, 2110 and the at least one foot support 12, 2112 may be further finely adjusted.

The position of at least one of the at least one knee support apparatus 10, 2110 and the at least one foot support apparatus 12, 2112 is capable of being finely adjusted with minimal manipulation of the patient's anatomy. The at least one directional guide 34 of each of the at least one knee support apparatus 10, 2110 and the at least one foot support apparatus 12, 2112 may be selected from the group consisting of a track, a rail, a rack, a slot, and combinations thereof. The at least one locator 42 of each of the at least one knee support apparatus 10, 2110 and the at least one foot support apparatus 12, 2112 is configured to receive at least one pin or at least one disc located on the target modality. The at least one locator 42 of each of the at least one knee support apparatus 10, 2110 and the at least one foot support 12, 2112 apparatus is configured to receive pins of a conventional locating bar 18.

The at least one of the at least one knee support apparatus 10, 2110 and the at least one foot support apparatus 12, 2112 is configured to be finely adjusted in discrete increments along the set distance of travel of the at least one directional guide of each of the at least one knee support apparatus and the at least one foot support apparatus. The at least one knee support apparatus 10, 2110 may have at least five discrete increments of fine adjustment and the at least one foot support apparatus 12, 2112 may have at least three discrete increments of fine adjustment. The at least one shuttle 36 of each of the at least one knee support apparatus 10, 2110 and the at least one foot support 12, 2112 apparatus comprises a series of locating features 43 spaced according to the discrete increments of fine adjustments along the set distance of travel of the at least one directional guide 34 of each of the at least one knee support apparatus 10, 2110 and the at least one foot support apparatus 12, 2112.

The at least one releasable lock of each of the at least one knee support apparatus 10, 2110 and the at least one foot support apparatus 12, 2112 incorporates a detent 48 which interfaces with the series of locating features 43 incorporated in the at least one shuttle 36 of each of the at least one knee support apparatus 10, 2110 and the at least one foot support apparatus 12, 2112. The detent 48 of the at least one releasable lock 16 of each of the at least one knee support apparatus 10, 2110 and the at least one foot support apparatus 12, 2112 inhibits the motion of the at least one shuttle 36 of each of the at the at least one knee support apparatus 10, 2110 and the at least one foot support apparatus 12, 2112 when the at least one releasable lock 16 of each of the at least one knee support apparatus 10, 2110 and the at least one foot support apparatus 12, 2112 is in the first engaged configuration and does not inhibit motion of the at least one shuttle 36 when the at least one releasable lock 16 of each of the at least one knee support apparatus 10, 2110 and the at least one foot support apparatus 12, 2112 is in the second disengaged configuration.

The least one releasable lock 16 further comprises at least one tensioner 46 configured to return the at least one releasable lock 16 to the first engaged configuration from the second disengaged configuration. The at least one tensioner 46 may be selected from the group consisting of a spring, an elastic band a belt and combinations thereof. The at least one knee support apparatus 10, 1128, 2110 further comprises: at least one top portion 28, 1128, 2128. The top portion 28, 1128, 2128 is configured to support the patient's legs at the area around the popliteal fossa. The knee support also comprises least one base portion, 32, 1132, 2132 that is removably attached to the at least one top portion 28, 1128, 2128, and is additionally coupled to the at least one directional guide 34, the at least one locator 42, the at least one shuttle 34, and the at least one releasable lock 16. The at least one base portion 32, 1132, 2132 is configured to be oriented in at least two different orientations. The at least one base portion 32, 1132, 2132 is configured to have a first height in a first orientation and a second height in a second orientation.

The at least one foot support apparatus 12, 2112 further comprises at least one tilting portion 54, 2154 including the at least one support and wherein the at least one foot support 12, 2112 is further configured to be disposed at different discrete angles along a range, and comprises a lock 56, 2156 configured to secure the at least one tilting portion 54, 2154 at a desired discrete angle; and at least one base portion 60, 2160 coupled to the at least one tilting portion, 54, 2154 and additionally coupled to the at least one directional guide 34, the at least one locator 42, the at least one shuttle 36, and the at least one releasable lock 16.

The at least one knee support apparatus 10, 2110 and the at least one foot support apparatus 12, 2112 are configured such that at least one of the gross position, fine position adjustment, height, or angle of each of the at least one knee support apparatus 10, 2110 and the at least one foot support apparatus 12, 2112 is capable of being selected independently of the gross position, fine position adjustment, height, or angle of the at least one knee support apparatus 10, 2110 and the at least one foot support apparatus 12, 2112. The at least one knee support apparatus 10, 2110 and the at least one foot support apparatus 12, 2112 may be configured such that at least one of the gross position, the fine position adjustment, the height, or the angle is individually adjustable for each limb of the patient.

A knee support 12, 2112 comprising the following components is provided: At least one support 12, 2112 is configured to support the patient's legs at an area around the popliteal fossa. At least one locator 42 is configured to locate the knee support 12, 2112 to a patient table 14 of a target modality. At least one directional guide 34 having a set distance of travel is provided. At least one shuttle 36 coupled to the at least one support 12, 2112, is configured to slidably adjust the support 12, 2112 along the at least one directional guide 34. At least one releasable lock 16 is configured to restrict the movement of the at least one shuttle 36 along the at least one directional guide 34 in a first engaged configuration, and enable movement of the at least one shuttle along the at least one directional guide in a second disengaged configuration.

The knee support 12, 2112 may further comprise at least one top 28, 2128 wherein the top portion 28, 2128 is configured to support the patient's legs at the area around the popliteal fossa; and at least one base portion 32, 2132 wherein the base portion 32, 2132 is removably attached to the at least one top portion 28, 2128, and is additionally coupled to the at least one directional guide 34 the at least one locator 42, the at least one shuttle 36, and the at least one releasable lock 16. The knee support 12, 2112 may be composed of materials which are compatible with a magnetic resonance imaging (MRI) environment.

The at least one base portion 32, 2132 of the knee support 12, 2112 comprises protrusions 62 to be received by corresponding apertures 64 in the at least one top portion 28, 2128. The knee support 12, 2112, wherein the at least one base portion 32, 2132 of the knee support 12, 2112 is configured to be oriented in at least two different orientations. The at least one base portion 32, 2132 of the knee support 12, 2112 is configured such that it will be at a first height in a first orientation and at a second height in a second orientation.

A method for utilizing a support system 100, 2100 configured to support the lower extremities of a patient is provided. The method comprises the following steps:

Placing locators 42 of at least one bottom portion 32, 2132 of at least one knee support 10, 2110 and a foot support 12, 2112 onto indexing structures 18 of a patient table 14 of an imaging or treatment modality such that the knee support 10, 2110 and the foot support 12, 2112 define a space 52, 2152 configured to accommodate the length of the patient's lower legs;

Selecting an orientation for the at least one bottom portion 32, 2132 of the at least one knee support 10, 2110;

Placing at least one top portion 28, 2128 of the at least one knee support 10, 2110 onto the at least one bottom portion 32, 2132 of the at least one knee support 10, 2110;

Positioning the patient on the support system 100, 2100;

Disengaging the at least one releasable lock 16 on the knee support 10, 2110;

Slidably adjusting the knee support 10, 2110 along a direction defined by the directional guide 34 of the at least one knee support 10, 2110 to a desired discrete position along the set distance;

Reengaging the at least one releasable lock 16 on the knee support 10, 2110;

Disengaging the at least one releasable lock 16 on the foot support 12, 2112;

Adjusting the position along the at least one directional guide 34 of at least one tilting portion 54, 2154 of the foot support 12, 2112;

Locking the tilting portion 54 of the at least one foot support 12, 2112 in a desired position along the at least one directional guide 34 of the at least one foot support 12, 2112;

Adjusting the at least one tilting portion 54, 2154 of the foot support 12, 2112 to a desired discrete angle position; and Locking the tilting portion 54 of the foot support 12, 2112 in the desired discrete angle position.

Generally, this invention provides various aspects and embodiments. In accordance with one aspect of the present invention, a support apparatus configured to support the anatomy of a patient, for example during radiotherapy and imaging procedures, is provided. In a preferred embodiment, all the components of said support apparatus are composed of materials which are compatible with magnetic resonance imaging environments. The support apparatus first includes at least one support, configured to support the anatomy of the patient. In an embodiment, this support may be composed of a rigid material, such as a rigid polymer. In an alternate embodiment, the support may be composed of a deformable material for additional patient comfort and to further conform to the patient's anatomy. The support apparatus includes at least one indexing feature configured to removably locate to a patient table of an imaging or treatment modality. In preferred embodiments, the indexing feature may be configured to receive a conventional indexing structure of a patient table of a target imaging or treatment modality (for example, a locating bar and corresponding recess in the modality, integrated discs, and other attachment mechanisms known to a person having skill in the art).

The support apparatus additionally includes at least one directional guide running parallel to a direction relative to the patient table, said directional guide having a set distance of travel. In a preferred embodiment, the directional guide may be a track, a rail, a rack, or other similar structure known to a person having ordinary skill in the art. In a further preferred embodiment, the direction is in the superior/inferior or longitudinal direction of the patient table. The support apparatus further includes at least one shuttle configured to slidably adjust the support apparatus along the at least one directional guide. The support apparatus further includes a releasable lock configured to resist the motion of the at least one shuttle in a first engaged position and enable motion of the at least one shuttle in the direction of the at least one directional guide in a second disengaged position. In preferred embodiment, this releasable lock is operable with only one hand.

The support apparatus is so configured such that a clinician may select the gross position of the support apparatus by locating the at least one indexing structure on the patient table of the imaging or treatment modality. If further fine adjustment of the patient's anatomy is desired, the clinician is able to disengage the releasable lock and slidably adjust the support apparatus along the direction of the directional guide, with minimal need to manipulate the patient's anatomy from the support apparatus or disturb the gross position of the support apparatus. This support apparatus may further include features which adjust either the height of the support apparatus or the angle of the support apparatus, further accommodating additional fine adjustments to the position of the patient's anatomy. These fine adjustment capabilities of the support system enable enhanced patient comfort, setup reproducibility, and workflow efficiency.

In a preferred embodiment, the at least one shuttle may additionally be configured to provide discrete adjustment increments along the direction of the at least one directional guide. In a further preferred embodiment, the discrete adjustment increments are achieved through the use of locating features integrated into the at least one shuttle. In a still further preferred embodiment, the locating features are a system of projections and recesses which interface with at least one corresponding structure on the at least one releasable lock, for example a tooth or other projection. In a preferred embodiment, the number of locating features correspond with the number of discrete increments for adjustment in the direction provided by the at least one directional guide. When slidably adjusting the support apparatus in the direction provided by the at least one directional guide, the releasable lock is disengaged to permit the movement of the at least on shuttle along the at least one track. The clinician is then enabled to slidably adjust the support apparatus as desired. When the clinician is satisfied with the superior-inferior position, the clinician reengages the at least one releasable lock, which disposes the tooth into a discrete increment provided by recesses of the locating features, thereby securing support apparatus in the desired fine adjustment position. The interface between the tooth and the locating features provide haptic feedback to the clinician as to whether the shuttle is appropriately disposed in one of the discrete adjustment increments. In another preferred embodiment, the support apparatus additionally includes visual indication of the discrete adjustment increments. The releasable lock may additionally include at least one tensioner (for example a spring, an elastic band or belt, a compressible member, or other structure known to one having skill in the art) which resists the disengagement of the releasable lock, such that once the clinician finishes the fine adjustment they can discontinue manipulating the releasable lock in order to have the releasable lock return to its engaged configuration, which will also dispose a tooth into one of the locating features. In a further preferred embodiment, the releasable lock is configured such that it may be pulled or pushed by the clinician in order to disengage the releasable lock. In this embodiment, a plurality of tensioners would exist to resist the disengagement of the releasable lock in either direction of manipulation, with the same automatic return of the releasable lock to its engaged position which additionally disposes the tooth of the releasable lock into the locating features of the shuttle.

According to a second aspect of the invention, a support system is provided with a plurality of support devices, wherein at least one of the support devices is a support apparatus as described in the foregoing aspect of the present invention, with at least one support apparatus of the support system being capable of being adjusted with respect to at least one of gross position, fine adjustment, height, and/or angle of the patient's anatomy, which may further be independently adjusted.

According to a third aspect of the invention, an exemplary support system is provided. This exemplary support system is configured to support the lower extremities of a patient. This support system includes at least one knee support apparatus and at least one foot support apparatus, each of which may be used together or independently in order to customize the support needed for the particular procedure. In a preferred embodiment, both the at least one knee support and at least one foot support are intended to separately removably locate to the patient table of the imaging or radiotherapy modality through locators disposed on each of the knee support apparatus and foot support apparatus which correspond to indexing structures appropriate to the target imaging or treatment modality. When used together to form the support system, the knee support and foot support define a space which accommodates the general length of the patient's lower legs. In a preferred embodiment, all components of the support system are compatible with a magnetic resonance imaging environment.

The knee support apparatus includes at least one support configured to support the patient's legs in the area surrounding the popliteal fossa. The knee support is further configured to accommodate at least one locator corresponding to an indexing structure on the patient table of the target modality, which removably locates the knee support apparatus to the patient table of the modality. The knee support apparatus further includes at least one directional guide which has a set distance of travel in a direction relative to the patient table of the target modality. The knee support apparatus also includes at least one shuttle, which allows the knee support apparatus to be slidably adjusted along the set distance of travel of the at least one directional guide. The knee support apparatus further includes at least one releasable lock which restricts motion of the knee support apparatus in a first engaged configuration and enables motion of the knee support apparatus in a second disengaged configuration. In a further preferred embodiment, the knee support apparatus may optionally enable the height of the knee support apparatus to be selected. The at least one support of the knee support apparatus may further comprise The foot support apparatus includes at least one base portion. The at least one base portion is configured to accommodate at least one indexing structure which removably secures the knee support to the patient table of the modality. The at least one base portion further has at least one tilting portion. The tilting portion further has a member configured to be disposed at different discrete angles along a range and having discrete indexing points defining those angles. The tilting portion is then configured to be releasably locked at the desired position. The tilting portion also has at least one heel support cup configured to support the heel and sole of the patient's foot while the device is in operation. In a preferred embodiment, the foot support apparatus is further configured to be slidably adjusted, and further comprises its own at least one directional guide which has a set distance of travel in a direction relative to the patient table of the target modality, at least one shuttle, which allows the foot support apparatus to be slidably adjusted along the set distance of travel of the at least one directional guide, and at least one releasable lock which restricts motion of the foot support apparatus in a first engaged configuration and enables motion of the foot support apparatus in a second disengaged configuration. The tilting portion of the foot support may be further adjusted along a range of discrete angles and releasably locked in order to maintain the desired position.

When used on the patient table of an appropriate imaging or treatment modality, the support system is configured to allow the clinician to independently adjust the knee support apparatus and foot support apparatus for optimal positioning of the patient for the target procedure. The gross position of the knee support apparatus and foot support apparatus are determined by the clinician and achieved via the use of the locators which correspond to indexing structures appropriate to the modality. The support system also allows the fine adjustment of each of the at least one knee support apparatus and at least one foot support apparatus without removal or addition of any components and with minimal manipulation of the patient's anatomy or gross position of the knee support apparatus and/or foot support apparatus on the modality. Both the knee support apparatus and the at least one tilting portion of the foot support apparatus may be slidably positioned along their respective set distances of travel in the direction of their respective directional guides, and then releasably locked in order to maintain their respective desired positions. In a preferred embodiment the knee support features height adjustment capabilities. In a further preferred embodiment, the support system is configured such that at least one of the gross position, fine position adjustment, height adjustment, or angular adjustment is individually adjustable for each leg. These fine adjustment capabilities of the support system enable enhanced patient comfort, setup reproducibility, and workflow efficiency.

In a further preferred embodiment, the knee support apparatus and the foot support apparatus may further incorporate discrete adjustment increments along the direction of the at least one directional guide. In a further preferred embodiment, the discrete adjustment increments are achieved through the use of locating features integrated into the at least one shuttle of each of the knee support apparatus and/or the at least one foot support apparatus. In a still further preferred embodiment, the locating features are a system of projections and recesses which interface with at least one corresponding structure on the at least one releasable lock, for example a tooth or other projection. In a preferred embodiment, the number of locating features correspond with the number of discrete increments for adjustment in the direction provided by the at least one directional guide of each of the at least one knee support apparatus and/or the at least one foot support apparatus, preferably at least three discrete increments for either the at least one knee support apparatus and the at least one foot support apparatus. In yet a further preferred embodiment, the knee support apparatus features at least five discrete increments, and the foot support apparatus features at least three discrete increments. When slidably adjusting either the knee support apparatus or foot support apparatus in the direction provided by their respective at least one directional guide, their respective releasable lock is disengaged to permit the movement of their respective at least on shuttle along their respective at least one directional guide. The clinician is then enabled to slidably adjust the knee support apparatus and/or foot support apparatus as desired. When the clinician is satisfied with the fine position of the device, the clinician reengages the respective at least one releasable lock of the at least one knee support apparatus and/or foot support apparatus, which disposes its tooth into a discrete increment provided by recesses of the locating features of the respective shuttle, thereby securing the at least one knee support apparatus and/or foot support apparatus in the desired fine adjustment position. The interface between the tooth and the locating features provide haptic feedback to the clinician as to whether the shuttle is appropriately disposed in one of the discrete adjustment increments. In another preferred embodiment, the at least one knee support apparatus and/or foot support apparatus additionally includes visual indication of their respective discrete adjustment increments. The releasable lock of either or both the at least one knee support apparatus or the at least one foot support apparatus may additionally include at least one tensioner (for example a spring, an elastic band or belt, a compressible member, or other structure known to one having skill in the art) which resists the disengagement of the respective at least one releasable lock, such that once the clinician finishes the fine adjustment they can discontinue manipulating the releasable lock in order to have the releasable lock return to its engaged configuration, which will also dispose its tooth into one of the locating features. In a further preferred embodiment, the releasable lock is configured such that it may be pulled or pushed by the clinician in order to disengage the releasable lock. In this embodiment, a plurality of tensioners would exist to resist the disengagement of the releasable lock in either direction of manipulation, with the same automatic return of the releasable lock to its engaged position which additionally disposes the tooth of the releasable lock into the locating features of the respective shuttle.

In accordance with another aspect of the invention, a knee support and foot support configured to support the lower extremities of the patient is provided for use with the patient tables of various imaging and treatment modalities.

The knee support includes at least one top portion configured to support the patient's legs in the area surrounding the popliteal fossa. The knee support is further configured to accommodate at least one indexing structure which removably secures the knee support to the patient table of the modality. The knee support further includes at least one directional guide mechanism, which allows the knee support to slide in discrete increments along a set distance in the superior-inferior direction relative to the at least one indexing structure. The knee support further includes at least one releasable lock which releasably locks the knee support along the superior-inferior direction.

In a preferred embodiment, the knee support includes at least one top portion and at least on base portion. The at least one top member is configured to support the patient's legs in the area surrounding the popliteal fossa. The at least one top member is optionally removably attached to the at least one bottom member. The at least one bottom member is further configured to accommodate at least one indexing structure, which removably secures the knee support to the patient table of the modality. The knee support further includes at least one track mechanism allowing the at least one top member and the at least one bottom member to slide in discrete increments along a set distance in the superior-inferior direction. The knee support further includes at least one releasable lock, which releasably locks the knee support at the desired position along the superior-inferior direction.

In a further preferred embodiment, the at least one bottom member features protrusions to be received by corresponding holes in the at least one top member. In this embodiment, the at least one bottom member is configured to be oriented multiple different ways. Changing the orientation of the bottom member results in adjustment of the height of the support. In a preferred embodiment, the bottom member has at least two orientations, such that it will be a first height in a first configuration and a second height in a second configuration. In a further preferred embodiment, the bottom member is a single molded piece where the two orientations can be alternately selected by flipping the structure over. The at least one bottom member is further configured to accommodate at least one indexing structure which removably secures the knee support to the patient table of the modality. In a preferred embodiment, the locating structures are at least two recesses to accommodate pins from a bar attached to the target modality. The knee support further has at least one track of a set distance and at least one shuttle allowing the at least one bottom member to slide in multiple discrete increments along a set distance in the superior-inferior direction. In a preferred embodiment the at least one track and at least one shuttle allow at least five discrete increments along its set distance in the superior-inferior direction. In a further preferred embodiment, the at least five discrete increments are approximately 35 millimeters apart.

The knee support further has at least one releasable lock, which releasably locks the knee support at the desired position along the superior-inferior direction. The at least one releasable lock, in a preferred embodiment, is configured to be easily operable with only one hand. The releasable lock interacts with the at least one shuttle by restricting its motion in a first engaged configuration and releasing the at least one shuttle to move along the direction defined by the at least one track in a second disengaged configuration. The at least one shuttle has a number of locating features. The locating features are a system of projections and recesses which interface with at least one corresponding structure on the at least one releasable lock. In a preferred embodiment, the number of locating features correspond with the number of discrete increments for adjustment in the superior-inferior direction. When slidably adjusting the knee support in the superior-inferior direction, the releasable lock is disengaged to permit the movement of the at least on shuttle along the at least one track. The locating features provide haptic feedback to the clinician as to whether the shuttle is appropriately disposed in one of the discrete adjustment increments. In another preferred embodiment, the knee support additionally includes visual indication of the discrete adjustment increments which is usable regardless of height orientation of the at least one bottom member. When the clinician is satisfied with the superior-inferior position, the clinician reengages the at least one releasable lock, securing the knee support in the desired position.

The foot support includes at least one base portion. The at least one base portion is configured to accommodate at least one indexing structure which removably secures the foot support to the patient table of the modality. The at least one base portion further includes at least one tilting portion. The tilting portion further has a member configured to be disposed at different discrete angles along a range. In a preferred embodiment, the tilting portion has at least 3 discrete indexing points defining those angles. In a further preferred embodiment, the at least three indexing points are configured to be 5 degrees apart. The tilting portion is then configured to be releasably locked at the desired discrete angle position. The tilting portion further comprises at least one heel support cup configured to support the heel and sole of the patient's foot while the device is in operation. The base portion further includes at least one track of a set distance and at least one shuttle to slide the whole tilting portion in discrete increments along said set distance in the superior-inferior direction. In a preferred embodiment, the track includes at least three discrete increments for superior-inferior adjustment. The base portion further includes a releasable lock to secure the tilting portion in the superior-inferior direction.

When used on the patient table of an appropriate imaging or treatment modality, the support system is configured to allow the clinician to adjust the knee support and foot support for optimal positioning of the patient for the target procedure. The knee support and foot support preferably are able be used independently of one another to further customization of the patient positioning. The gross position of the knee support and foot support are achieved via the use of the indexing structures appropriate to the modality (for example a locating bar and corresponding recess in the modality, integrated discs, and other attachment mechanisms known to a person having skill in the art). The height of the knee support is then selected from one of the multiple configurations of the bottom member. The support system also allows the fine adjustment of each of the knee support and foot support without removal or addition of any components and without changing the gross position of the knee support and/or foot support on the modality. Both the knee support and the at least one tilting portion of the foot support may be slidably positioned in discrete increments along a range in the superior-inferior direction and then releasably locked in order to maintain the desired position. The tilting portion of the foot support may be further adjusted along a range of discrete angles and releasably locked in order to maintain the desired position. These fine adjustment capabilities of the support system enable enhanced patient comfort, setup reproducibility, and workflow efficiency.

In accordance with yet another aspect of the invention, a method for utilizing the support system of the present invention is provided. The method includes the following steps:

a) Placing locators of at least one bottom portion of at least one support apparatus onto indexing structures of a patient table of an imaging or treatment modality to select the gross position of the support apparatus;

c) Disengaging at least one releasable lock on the support apparatus;

c) Slidably adjusting the support apparatus along a direction defined by at least one directional guide of the at least one support apparatus to a desired discrete position along the set distance of travel of the directional guide;

d) Reengaging the at least one releasable lock on the support apparatus.

According to an embodiment, the method may further comprise additional steps of selecting an orientation for a base portion of the at least one support apparatus and then placing at least one top portion configured to support the patient's anatomy onto the base portion of the at least one support apparatus.

According to another embodiment, a fine adjustment of the support apparatus may be accomplished without removing the anatomy of the patient from the support apparatus and the fine adjustment may be accomplished without changing a gross position of the support apparatus.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A support apparatus configured to support a patient's anatomy, the support apparatus comprising:

at least one support configured to support a patient's anatomy, the at least one support comprising at least one base portion removably attached to at least one top portion;

at least one locator configured to removably locate the support apparatus to a patient table of a target modality;

at least one directional guide having a set distance of travel;

at least one shuttle coupled to the at least one support, configured to slidably adjust the support along the at least one directional guide;

at least one releasable lock configured to restrict movement of the at least one shuttle along the at least one directional guide in a first engaged configuration, and enable movement of the at least one shuttle along the at least one directional guide in a second disengaged configuration;

wherein a gross position of the support apparatus is selected by locating the at least one locator to a corresponding structure on the patient table of the target modality and wherein a position of the support apparatus may be finely adjusted in discrete increments along the set distance of travel of the at least one directional guide; and wherein the at least one base portion is additionally directly or indirectly coupled to the at least one directional guide, the at least one locator, the at least one shuttle, and the at least one releasable lock, wherein the at least one base portion has irregular geometry, such that the at least one base portion is configured to be oriented in at least a first orientation and a second orientation, and wherein the irregular geometry of the at least one base portion permits the at least one base portion to be positioned at a first height in the first orientation and at a second height in the second orientation.

2. The support apparatus of claim 1, wherein the position of the support apparatus is capable of being finely adjusted with minimal manipulation of the patient's anatomy.

3. The support apparatus of claim 1, wherein the at least one directional guide is selected from the group consisting of a track, a rail, a rack, a slot, and combinations thereof.

4. The support apparatus of claim 1, wherein the at least one shuttle incorporates a series of locating features spaced according to the discrete increments of fine adjustments along the set distance of travel of the at least one directional guide.

5. The support apparatus of claim 4, wherein the at least one releasable lock incorporates a detent which interfaces with the locating features incorporated in the at least one shuttle and wherein the detent of the at least one releasable lock inhibits the motion of the at least one shuttle when the at least one releasable lock is in the first engaged configuration and does not inhibit motion of the at least one shuttle when the at least one releasable lock is in the second disengaged configuration.

6. The support apparatus of claim 4, wherein the at least one releasable lock comprises at least one tensioner configured to return the at least one releasable lock to the first engaged configuration from the second disengaged configuration.

7. The support apparatus of claim 1, wherein the support apparatus is additionally capable of adjusting an angle of a patient's anatomy.

8. The support apparatus of claim 1, wherein the support apparatus is configured to support the lower extremities of the patient.

9. The support apparatus of claim 1 wherein the support apparatus is a knee support wherein:

the at least one support is configured to support the patient's legs at an area including the popliteal fossa, the top portion is configured to support the patient's legs at the area including the popliteal fossa.

10. The support apparatus of claim 9, wherein the at least one top portion comprises protrusions to be received by corresponding apertures in the at least one base portion.

11. The support apparatus of claim 9, wherein the at least one shuttle has at least five discrete increments along the set distance of travel of the at least one directional guide.

12. The support apparatus of claim 9, wherein the at least one support further comprises at least one visual indicator for the fine adjustment position of the at least one support, wherein the visual indicator is configured to be readable in the first orientation and in the second orientation.

13. A method for configuring a support apparatus to support the lower extremities of a patient prior to use, the method comprising:

placing locators of at least one bottom portion of at least one support apparatus onto indexing structures of a patient table of an imaging or treatment modality to select the gross position of the support apparatus;

disengaging at least one releasable lock on the support apparatus;

slidably adjusting the support apparatus along a direction defined by at least one directional guide of the at least one support apparatus to a desired discrete position along the set distance of travel of the directional guide;

reengaging the at least one releasable lock on the support apparatus; and changing a height of the support apparatus by changing an orientation of a base portion of the support apparatus.

14. The method of claim 13, further comprising selecting an orientation for a base portion of the at least one support apparatus; and placing at least one top portion configured to support the patient's anatomy onto the base portion of the at least one support apparatus.

15. The method of claim 13, wherein a fine adjustment of the support apparatus is accomplished without removing the anatomy of the patient from the support apparatus and wherein the fine adjustment is accomplished without changing a gross position of the support apparatus.

* * * * *